US010328147B2

(12) United States Patent
Kousoulas

(10) Patent No.: US 10,328,147 B2
(45) Date of Patent: Jun. 25, 2019

(54) HERPES SIMPLEX VIRUS TYPE-1(HSV-1) VACCINE STRAIN VC2 GENERATING AN ANTI-EHV-1 IMMUNE RESPONSE

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventor: Konstantin G. Kousoulas, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 15/928,377

(22) Filed: Mar. 22, 2018

(65) Prior Publication Data

US 2018/0271974 A1 Sep. 27, 2018

Related U.S. Application Data

(60) Provisional application No. 62/476,086, filed on Mar. 24, 2017, provisional application No. 62/478,349, filed on Mar. 29, 2017.

(51) Int. Cl.

| | |
|---|---|
| ***A61K 39/00*** | (2006.01) |
| ***A61K 39/39*** | (2006.01) |
| ***A61P 31/22*** | (2006.01) |
| ***C07K 16/08*** | (2006.01) |
| ***C12N 15/85*** | (2006.01) |
| ***C12N 15/86*** | (2006.01) |
| ***A61K 39/245*** | (2006.01) |
| ***C07K 14/005*** | (2006.01) |
| ***C07K 14/035*** | (2006.01) |
| ***C12N 15/869*** | (2006.01) |

(52) U.S. Cl.

CPC ............ *A61K 39/245* (2013.01); *A61K 39/39* (2013.01); *A61P 31/22* (2018.01); *A61K 2039/5252* (2013.01); *A61K 2039/552* (2013.01); *A61K 2039/55566* (2013.01); *A61K 2300/00* (2013.01); *C07K 14/005* (2013.01); *C07K 14/035* (2013.01); *C07K 16/087* (2013.01); *C12N 15/85* (2013.01); *C12N 15/86* (2013.01); *C12N 15/869* (2013.01); *C12N 2710/16634* (2013.01); *C12N 2710/16643* (2013.01)

(58) Field of Classification Search

CPC .. A61K 2300/00; A61K 39/12; A61K 39/245; A61K 35/763; A61K 2039/6075; A61K 35/76; A61K 35/766; A61K 39/42; A61K 39/205; A61K 2121/00; A61K 39/295; A61K 39/39; A61K 2039/552; A61K 2039/55566; A61K 2039/5252; C12N 15/86; C12N 2710/16634; C12N 2710/16643; C12N 15/85; C12N 15/869; C12N 2710/16662; C12N 2710/16671; C12N 2710/00; C12N 2710/00034; C12N 2710/16043; C12N 2710/16611; C12N 2710/16721; C12N 2830/60; C07K 14/005; C07K 14/035; C07K 16/087; A61P 31/22

See application file for complete search history.

(56) References Cited

U.S. PATENT DOCUMENTS 5,470,718 A 11/1995 O'Callaghan

FOREIGN PATENT DOCUMENTS

WO 2015172033 A1 11/2015

OTHER PUBLICATIONS

Yadav et al., Evaluation of the T cells and costimulatory molecules in the protective efficacy of 30 kDa secretory protein against experimental tuberculosis, Immunology and Cell Biology (2001) 79, 207-212.

Yeo et al., Equine herpesvirus type 1 infection induces procoagulant activity in equine monocytes,Veterinary Research (2013) 44(16): 1-14.

Zhang et al., Protective immunity against equine herpesvirus type-1 (EHV-1) infection in mice induced by recombinant EHV-1 gD, Virus Research(1998) 56: 11-24.

International Search Report and Written Opinion for International Application No. PCT/US18/23750 dated Jun. 7, 2018, 14 pages.

Allen et al., Major Histocompatibility Complex Class I-Restricted CytotoxicT-Lymphocyte Responses in Horses Infected withEquine Herpesvirus 1, Journal of Virology, Jan. 1995, 69(1) 606-612.

Allen et al., Equid herpesvirous 1 and equid herpesvirus 4 infections, Infection Dis. Livestock (2004) 76: 829-859.

(Continued)

*Primary Examiner* — Rachel B Gill

(74) *Attorney, Agent, or Firm* — Thomas|Horstemeyer, LLP

(57) ABSTRACT

Embodiments of nucleic acids comprise a nucleotide sequence encoding a live-attenuated chimeric Herpes Simplex Virus Type-1 (HSV-1) VC2 virus and a nucleotide sequence encoding a heterologous polypeptide operably linked to a promoter. The nucleotide sequence encoding the heterologous polypeptide can be operably linked to a promoter encoding the glycoprotein D (gD) of Equine Herpesvirus-1 (EHV-1) or a fragment thereof. Also provided is a live-attenuated recombinant Herpes Simplex Virus Type-1 (HSV-1) VC2 virus comprising a nucleotide sequence encoding a nucleotide sequence encoding a heterologous polypeptide operably linked to a promoter.

6 Claims, 15 Drawing Sheets

Specification includes a Sequence Listing.

(56) References Cited

OTHER PUBLICATIONS

Allen et al., Prevalence of latent, neuropathogenic equine herpesvirus-1 inthe Thoroughbred broodmare population of central Kentucky, Equine vet. J. (2008) 40 (2): 105-110.
Azab et al., Glycoproteins D of Equine Herpesvirus Type 1 (EHV-1) and EHV-4Determine Cellular Tropism Independently of Integrins, J. Virol. (2012) 86: 2031-2044.
Bartels et al., In situ study on the pathogenesis and immune reaction of equine herpesvirus type 1(EHV-1) infections in mice, Immunology (1998) 93: 329-334.
Bartels et al., Comparative metabolism of ortho-phenylphenol inmouse, rat and man, Xenobiotica 1998 (28)(6): 579-594.
Bego et al., Development of an ELISA to detect Sin Nombre virus-specific IgMfrom deer mice (*Peromyscus maniculatus*), J. Virol. Methods (2008) 151: 204-210.
Abi Berger, Science commentary: Th1 and Th2 responses: what are they? BMJ (2000) 321: 424.
Breathnach et al., Equine herpesvirus-1 infection induces IFN-γ production byequine T lymphocyte subsets, Veterinary Immunology and Immunopathology (2005)103: 207-215.
Cantin et al., Role for Gamma Interferon in Control of Herpes SimplexVirus Type 1 Reactivation, Journal of Virology (1999) 73(4): 3418-3423.
Coxon et al., Fcγ RIII Mediates Neutrophil Recruitment to ImmuneComplexes: A Mechanism for Neutrophil Accumulation in Immune-Mediated Inflammation, Immunity, 2001 (14): 693-704.
Csellner et al., EHV-1 glycoprotein D (EHV-1 gD) is required for virus entryand cell-cell fusion, and an EHV-1 gD deletion mutantinduces a protective immune response in mice, Arch. Virol. (2000) 145: 2371-2385.
Ebrahimpoor et al., IgG1 and IgG2a Profile of Serum Antibodies to Leishmania majorAmastigote in BALB/c and C57BL/6Mice, Iran. J. Allergy Asthma Immunol. (2013) 12(4): 361-367.
Flowers et al., Equine Herpesvirus 1 Glycoprotein D: Mapping of theTranscript and a Neutralization Epitope, (1992) Journal of Virology, (1992) 66(11): 6451-6460.
Foote et al., Serum antibody responses to equine herpesvirus 1 glycoproteinD in horses, pregnant mares and young foals, Vet. Immunol. Immunopathol. (2005)105: 47-57.
Foote et al., Inoculation of mares and very young foals with EHV-1glycoproteins D and B reduces virus shedding followingrespiratory challenge with EHV-1, Vet. Immunol. Immunopathol. (2006) 111: 97-108.
Fossati et al., Fcγ receptors in autoimmune diseases, European Journal of Clinical Investigation (2001) 31, 821-831.
Frampton et al., Meningoencephalitis in Mice Infected with an Equine Herpesvirus 1 Strain KyARecombinant Expressing Glycoprotein I and Glycoprotein E, Virus Genes (2004) 29:1, 9-17.
Fuentealba et al., Protective Effects of Intranasal Immunization with Recombinant Glycoprotein D in Pregnant BALB/c Mice Challenged with Different Strains of Equine Herpesvirus 1, J. Comp. Pathol (2014) 151: 384-393.
Fuentealba et al., Production of equine herpesvirus 1 recombinant glycoprotein D anddevelopment of an agar gel immunodiffusion test for serologicaldiagnosis, J. Virol. Methods (2014) 202: 15-18.
Haeberle et al., Inducible Expression of Inflammatory Chemokines in RespiratorySyncytial Virus-Infected Mice: Role of MIP-1α in Lung Pathology, Journal of Virology, 2001 (75)(2): 878-890.
Hamano et al., Immune Complex and Fc Receptor-Mediated Augmentation of Antigen Presentation for in Vivo Th Cell Responses, J. Immunol. (2000) 164: 6113-6119.
Hannant et al., Responses of ponies to equid herpesvirus-1 ISCOM vaccination and challenge with virus of the homologous strain, Research in Veterinary Scienc, (1993) 54: 299-305.
Kochetov et al., Eukaryotic mRNAs encoding abundant and scarce proteins arestatistically dissimilar in many structural features, FEBS Letts. (1998) 440: 351-355.
Koyama et al., Comparative studies on the levels of serum IgG1 and IgG2a in susceptible B10.BR mice infected with different strains of the intestinal nematode parasite *Trichuris muris*, Parasitol. Res. (2001) 87: 570-572.
Kydd et al., Pre-infection frequencies of equine herpesvirus-1 specific,cytotoxic T lymphocytes correlate with protection against abortion following experimentalinfection of pregnant mares, Veterinary Immunology and Immunopathology (2003) 96: 207-217.
Kydd et al., The equine immune response to equine herpesvirus-1:The virus and its vaccines, Veterinary Immunology and Immunopathology (2006) 111: 15-30.
Laval et al., Equine Herpesvirus Type 1 Enhances Viral Replication in CD172a Monocytic Cells upon Adhesion to Endothelial Cells, Journal of Virology (2015) 89(21): 10912-10923.
Love et al., Characterization of the glycoprotein D gene products of equine herpesvirus 1 using a prokaryotic cell expression vector, Veterinary Microbiology, (1992)30: 387-394.
Ma et al., An Equine Herpesvirus Type 1 (EHV-1) Expressing VP2 and VP5 of Serotype 8 Bluetongue Virus (BTV-8) Induces Protection in a Murine Infection Model, PLoS One, (2012) 7(4): 1-9.
McCarthy et al., Proinflammatory Effects of Interferon Gamma in Mouse Adenovirus 1 Myocarditis, Journal of Virology, (2015) 89(1): 468-479.
McCaughan et al., Translational termination efficiency in mammals is influenced bythe base following the stop codon, Proc. Natl. Acad. Sci. (1995) 92: 5431-5435.
Mikloska et al., Alpha and Gamma Interferons Inhibit Herpes Simplex Virus Type 1 Infection and Spread in Epidermal Cells after Axonal Transmission, Journal of Virology (2001) 75(23): 11821-11826.
O'Flaherty et al., CD8+ T Cell Response to Gammaherpesvirus Infection Mediates Inflammation andFibrosis in Interferon Gamma Receptor-Deficient Mice, PLoS One (2015), 1-25.
Packiarajah et al., Immune responses and protective efficacy of recombinant baculovirus-expressed glycoproteins of equine herpesvirus 1(EHV-1) gB, gC and gD alone or in combinations in BALB/c mice, Veterinary Microbiology (1998) 61: 261-278.
Ruitenberg et al., DNA-mediated immunization with glycoprotein D of equine herpesvirus 1 (EHV-1) in a murine model of EHV-1 respiratory infection, Vaccine (1999) 17: 237-244.
Ruitenberg et al., Equine herpesvirus 1 (EHV-1) glycoprotein D DNA inoculation in horses with pre-existingEHV-1/EHV-4 antibody, Veterinary Microbiology,(2000)76: 117-127.
Ruitenberg et al., Equine herpesvirus 1 glycoprotein D expressed in Pichia pastoris is hyperglycosylated and elicits a protective immune response in the mouse model of EHV-1 disease, Virus Research (2001)79: 125-135.
Shin et al., Avaccine strategy that protects against genital herpes by establishing local memory T cells, Nature (2012) 491:463-467.
Smith et al., Severe Murine Lung Immunopathology Elicited by the Pathogenic Equine Herpesvirus 1 Strain RacL11 Correlates with Early Production of Macrophage Inflammatory Proteins 1α, 1β, and 2 and Tumor Necrosis Factor Alpha, J. Virol. (2000) 74: 10034-10040.
Soboll et al., Identification of equine herpesvirus-1 antigens recognized by cytotoxic T lymphocytes, Journal of General Virology (2003), 84, 2625-2634.
Song et al., Effect of aqueous extracts of Scutellaria baicalensis Georgi and Radix paeoniae Alba on the serum IgG1 and IgG2a of the periodontitis mice, Zhonghua Kou Qiang Yi Xue Za Zhi (2014) 49: 89-94.
Stanfield et al., A Single Intramuscular Vaccination of Mice with the HSV-1 VC2 Virus with Mutations in the Glycoprotein K and the Membrane Protein UL20 Confers Full Protection against Lethal Intravaginal Challenge with Virulent HSV-1 and HSV-2 Strains, PLoS One (2014) 9(10): 1-13.
Stanfield et al., Vaccination of rhesus macaques with the live-attenuated HSV-1 vaccineVC2 stimulates the proliferation of mucosal T cells and germinal centerresponses resulting in sustained production of highly neutralizingantibodies, Vaccine (2017) 35: 536-543.
Tischer et al., Two-step Red-mediated recombination for versatile high-efficiency markerless DNA manipulation in *Escherichia coli*, Biotechniques (2006) 40: 191-197.
Trapp et al., Potential of Equine Herpesvirus 1 as a Vector for Immunization, Journal of Virology, (2005) 79(9), 5445-5454.

(56) References Cited

OTHER PUBLICATIONS

Van Woensel et al., A mouse model for testing the pathogenicity of equine herpes virus-1 strains, Journal of Virological Metods (1995)54: 39-49.
Walker et al., Comparison of the pathogenesis of acute equine herpesvirus 1 (EHV-1) infection in the horseand the mouse model: a review, Veterinary Microbiology (1999) 68: 3-13.
Weerasinghe et al., Equine herpesvirus 1 glycoprotein D expressed in *E. coli* provides partial protection against equine herpesvirus infection in mice and elicits virus-neutralizing antibodies in the horse, Veterinary Immunology and Immunopathology (2006) 111: 59-66.
Wellington et al., Expression and characterization of equine herpesvirus 1 glycoprotein D in mammalian cell lines, Arch. Virol. (1996) 141: 1785-1793.
Paillot et al., (2017) Equine Vaccine: How, When and Why? Report of the Vaccinology Session, French Equine Veterinarians Association, 2016, Reims. Vaccines; 5: 46-57.
Minke et al., (2004) Equine Viral Vaccines: the Past, Present and Future. Veterinary Research; 35: 425-443.

SEQUENCE LISTING

<160> NUMBER OF SEQ ID NOS: 16

<210> SEQ ID NO 1
<211> LENGTH: 36
<212> TYPE: DNA
<213> ORGANISM: Artificial sequence
<220> FEATURE:
<223> OTHER INFORMATION: Primer P1 Template EHV-1 gD

<400> SEQUENCE: 1
aagcttgcgg ccgcgatgtc taccttcaag cttatg 36

<210> SEQ ID NO 2
<211> LENGTH: 33
<212> TYPE: DNA
<213> ORGANISM: Artificial sequence
<220> FEATURE:
<223> OTHER INFORMATION: Primer P2 Template EHV-1 gD

<400> SEQUENCE: 2
aagcttggat cccggaagct gggtatattt aac 33

<210> SEQ ID NO 3
<211> LENGTH: 75
<212> TYPE: DNA
<213> ORGANISM: Artificial sequence
<220> FEATURE:
<223> OTHER INFORMATION: Primer P3 Template pEPkan-S

<400> SEQUENCE: 3
cttggtgaat tcaacttccc acaaggagag catatgacat ggttgaagtt ctgaggatga 60
cgacgataag taggg 75

<210> SEQ ID NO 4
<211> LENGTH: 37
<212> TYPE: DNA
<213> ORGANISM: Artificial sequence
<220> FEATURE:
<223> OTHER INFORMATION: Primer P4 Template pEPkan-S

<400> SEQUENCE: 4
cttggtgaat tccaaccaat taaccaattc tgattag 37

<210> SEQ ID NO 5
<211> LENGTH: 73
<212> TYPE: DNA
<213> ORGANISM: Artificial sequence
<220> FEATURE:
<223> OTHER INFORMATION: Primer P5 Template CMV-14

<400> SEQUENCE: 5
gtggcgtgaa actcccgcac ctcttcggca agcgccttgt agaagcgcgt ccatgttgac 60
attgattatt gac 73

<210> SEQ ID NO 6
<211> LENGTH: 73
<212> TYPE: DNA
<213> ORGANISM: Artificial sequence
<220> FEATURE:
<223> OTHER INFORMATION: Primer P6 Template CMV-14

<400> SEQUENCE: 6
ttattgccgt catagcgcgg gttccttccg gtattgtctc cttccgtgtt aaggacaggg 60
aagggagcag tgg 73

-continued

<210> SEQ ID NO 7
<211> LENGTH: 24
<212> TYPE: DNA
<213> ORGANISM: Artificial sequence
<220> FEATURE:
<223> OTHER INFORMATION: Primer P7 Template EHV-1 gD

<400> SEQUENCE: 7
ggcgtgtacg gtgggaggtc tata 24

<210> SEQ ID NO 8
<211> LENGTH: 24
<212> TYPE: DNA
<213> ORGANISM: Artificial sequence
<220> FEATURE:
<223> OTHER INFORMATION: Primer P8 Template EHV-1 gD

<400> SEQUENCE: 8
atgccaacgt gtgcaacgcc tata 24

<210> SEQ ID NO 9
<211> LENGTH: 24
<212> TYPE: DNA
<213> ORGANISM: Artificial sequence
<220> FEATURE:
<223> OTHER INFORMATION: Primer P9 Template EHV-1 gD

<400> SEQUENCE: 9
ttatgaagcc caggcattcg caag 24

<210> SEQ ID NO 10
<211> LENGTH: 23
<212> TYPE: DNA
<213> ORGANISM: Artificial sequence
<220> FEATURE:
<223> OTHER INFORMATION: Primer P10 Template EHV-1 gD

<400> SEQUENCE: 10
aattatgcca acgtgtgcaa cgc 23

<210> SEQ ID NO 11
<211> LENGTH: 23
<212> TYPE: DNA
<213> ORGANISM: Artificial sequence
<220> FEATURE:
<223> OTHER INFORMATION: Primer P11 Template EHV-1 gD

<400> SEQUENCE: 11
ctggttcgtc tacgatggtg gaa 23

<210> SEQ ID NO 12
<211> LENGTH: 23
<212> TYPE: DNA
<213> ORGANISM: Artificial sequence
<220> FEATURE:
<223> OTHER INFORMATION: Primer P12 Template EHV-1 gD

<400> SEQUENCE: 12
aagtctgcac agaacggctt gac 23

<210> SEQ ID NO 13
<211> LENGTH: 12
<212> TYPE: PRT
<213> ORGANISM: Artificial sequence
<220> FEATURE:
<223> OTHER INFORMATION: Predicted MHC-1 binding peptide of mouse
allele H-2-Dd -continued

```
<400> SEQUENCE: 13

Lys Pro Pro Lys Thr Ser Lys Ser Asn Ser Thr Phe
1               5                   10


<210> SEQ ID NO 14
<211> LENGTH: 10
<212> TYPE: PRT
<213> ORGANISM: Artificial sequence
<220> FEATURE:
<223> OTHER INFORMATION: Predicted MHC-1 binding peptide of mouse
      allele H-2-Ld

<400> SEQUENCE: 14

Phe Pro Pro Pro Arg Tyr Asn Tyr Thr Ile
1               5                   10


<210> SEQ ID NO 15
<211> LENGTH: 15
<212> TYPE: PRT
<213> ORGANISM: Artificial sequence
<220> FEATURE:
<223> OTHER INFORMATION: Predicted MHC-2 binding peptide of mouse
      allele H2-IEd

<400> SEQUENCE: 15

Gly Val Ile Leu Tyr Val Cys Leu Arg Arg Lys Lys Glu Leu Lys
1               5                   10                  15


<210> SEQ ID NO 16
<211> LENGTH: 22
<212> TYPE: PRT
<213> ORGANISM: Artificial sequence
<220> FEATURE:
<223> OTHER INFORMATION: 3xFLAG peptide

<400> SEQUENCE: 16

Asp Tyr Lys Asp His Asp Gly Asp Tyr Lys Asp His Asp Ile Asp Tyr
1               5                   10                  15

Lys Asp Asp Asp Asp Lys
            20
```

HERPES SIMPLEX VIRUS TYPE-1(HSV-1) VACCINE STRAIN VC2 GENERATING AN ANTI-EHV-1 IMMUNE RESPONSE

CROSS REFERENCE TO RELATED APPLICATIONS

This application claims the benefit of U.S. Provisional Application No. 62/476,086 filed Mar. 24, 2017, and of U.S. Provisional Application No. 62/478,349, filed Mar. 29, 2017, both of which are incorporated herein by reference in their entireties.

SEQUENCE LISTING

This application contains a sequence listing filed in electronic form as an ASCII.txt file entitled "2222201080_ST25" created on Mar. 20, 2018. The content of the sequence listing is incorporated herein in its entirety.

TECHNICAL FIELD

The present disclosure is generally related to HSV-1-based vaccines for animal herpesvirus infections. The present disclosure is also generally related to HSV-1-based vaccines for equine herpesvirus infections.

BACKGROUND

Equine Herpesvirus-1 (EHV-1) belongs to the Alphaherpesvirinae subfamily and is an important ubiquitous enzootic equine pathogen causing epidemic abortion, perinatal mortality, respiratory disease, and occasionally neurological disease in horses, causing significant economic losses to the horse industry. EHV-1 infection elicits a local immune response at the primary site of replication, as well as systemic humoral and cellular immune responses. EHV-1 infection of naïve animals induces protective immunity against re-infection lasting 4 to 8 months after the initial acute infection (Trapp et al., (2005) *J. Virol.* 79: 5445-5454). EHV-1 viral glycoproteins facilitate multiple aspects of the viral lifecycle including mediation of the fusion of the viral envelope with cellular membranes, intracellular virion morphogenesis, egress, cell-to-cell spread, and virus-induced cell fusion. Thus, these proteins are major antigenic determinants for both humoral and cellular immune responses and have been utilized as subunit vaccines (Laval et al., (2015) *J. Virol.* doi:10.1128/JVI.01589-15; Fuentealba et al., (2014) *J. Virol. Methods* 202: 15-18; Fuentealba et al., (2014) *J. Comp. Pathol* 151: 384-393). Specifically, immunization with EHV-1 gD has been shown to generate protective immune responses in mice and horses (Fuentealba et al., (2014) *J. Virol. Methods* 202: 15-18, Packiarajah et al., (1998) *Vet. Microbiol.* 61: 261-278; Zhang et al., (1998) *Virus Res.* 56: 11-24; Azab & Osterrieder (2012) *J. Virol.* 86: 2031-2044; Weerasinghe et al., (2006) *Vet. Immunol. Immunopathol.* 111: 59-66; Foote et al., (2006) *Vet. Immunol. Immunopathol.* 111: 97-108; Foote et al., (2005) *Vet. Immunol. Immunopathol.* 105: 47-57; Ruitenberg et al., (2001) *Virus Res.* 79: 125-135). EHV-1 and HSV-1 glycoprotein gDs are required for entry into cells and cell-to-cell fusion, a function which is conserved in most, but not all alphaherpesviruses (Csellner et al., (2000) *Arch. Virol.* 145: 2371-2385).

Despite regular and widespread vaccination, outbreaks of EHV-1 continue to occur. Current commercial vaccines that contain inactivated virus confer only partial clinical and virological protection against EHV-1 respiratory infections, because they do not stimulate cellular immune responses, specifically cytotoxic T cells that can control cell-associated viremia and virus dissemination from the respiratory track (Kydd et al., (2006) *Vet. Immunol. Immunopathol.* 111: 15-30). Viral-vectored vaccines express antigens within the infected cell that can be presented via MHC class 1 (endogenous) and class II (exogenous) antigen-processing routes stimulating both humoral and cell-mediated immune responses (Yeo et al., (2013) *Vet. Res.* 44: 16).

SUMMARY

Briefly described, one aspect of the present disclosure encompasses embodiments of a recombinant nucleic acid comprising a nucleotide sequence encoding a live-attenuated chimeric Herpes Simplex Virus Type-1 (HSV-1) VC2 virus and a nucleotide sequence encoding a heterologous polypeptide operably linked to a promoter.

In some embodiments of this aspect of the disclosure the nucleotide sequence encoding the heterologous polypeptide can be operably linked to a promoter encoding the glycoprotein D (gD) of Equine Herpesvirus-1 (EHV-1) or a fragment thereof.

Another aspect of the disclosure encompasses embodiments of a live-attenuated recombinant Herpes Simplex Virus Type-1 (HSV-1) VC2 virus comprising a nucleotide sequence encoding a nucleotide sequence encoding a heterologous polypeptide operably linked to a promoter.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

Still another aspect of the disclosure encompasses embodiments of a viral vaccine comprising a physiologically acceptable carrier and an immunogenic amount of a chimeric Herpes Simplex Virus Type-1 (HSV-1) VC2 virus comprising a nucleotide sequence encoding a heterologous polypeptide operably linked to a promoter.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

In some embodiments of this aspect of the disclosure the physiologically acceptable carrier can comprise an adjuvant.

Yet another aspect of the disclosure encompasses embodiments of a method of generating an antibody in an animal, wherein said method comprises the step of administering to an animal a pharmaceutically acceptable composition comprising a chimeric live-attenuated Herpes Simplex Virus Type-1 (HSV-1) VC2 virus, said virus comprising a nucleotide sequence encoding a heterologous polypeptide operably linked to a promoter a physiologically acceptable carrier.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

Still yet another aspect of the disclosure encompasses a method of generating an immune response in an animal, wherein said method comprising the step of administering to an animal a pharmaceutically acceptable composition comprising a chimeric live-attenuated Herpes Simplex Virus Type-1 (HSV-1) VC2 virus, said virus comprising a nucleotide sequence encoding a heterologous polypeptide operably linked to a promoter a physiologically acceptable carrier.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 9A is a graph illustrating in vitro analysis of a humoral immune response before challenge. Colorimetric ELISA was based on analysis of EHV-1 reactive polyclonal IgG1.

FIG. 9B is a graph illustrating in vitro analysis of a humoral immune response after challenge. Colorimetric ELISA was based on analysis of EHV-1 reactive polyclonal IgG1.

FIG. 9C is a graph illustrating in vitro analysis of a humoral immune response before challenge. Colorimetric ELISA was based on analysis of EHV-1 reactive polyclonal IgG2a.

FIG. 9D is a graph illustrating in vitro analysis of a humoral immune response after challenge. Colorimetric ELISA was based on analysis of EHV-1 reactive polyclonal IgG2a.

FIG. 9E is a graph illustrating in vitro analysis of a humoral immune response before challenge. Colorimetric ELISA was based on analysis of EHV-1 reactive polyclonal IgG2b.

FIG. 9F is a graph illustrating in vitro analysis of a humoral immune response after challenge. Colorimetric ELISA was based on analysis of EHV-1 reactive polyclonal IgG2b.

FIG. 9G is a graph illustrating in vitro analysis of a humoral immune response before challenge. Colorimetric ELISA was based on analysis of EHV-1 reactive polyclonal IgGM.

FIG. 9H is a graph illustrating in vitro analysis of a humoral immune response after challenge. Colorimetric ELISA was based on analysis of EHV-1 reactive polyclonal IgGM.

DETAILED DESCRIPTION

Figure 1A:
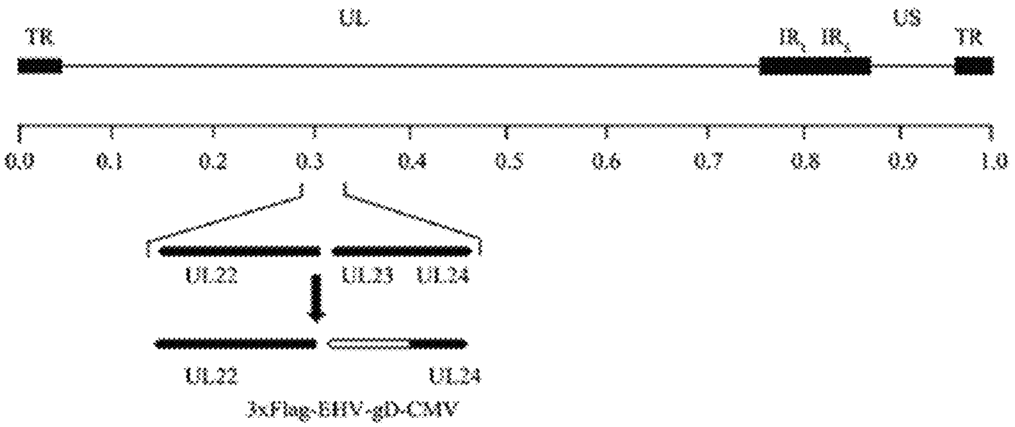
FIG. 1A illustrates a schematic of the VC2-EHV-1gD genome showing the insertion of the EHV-1 gD in-place of the UL23 (thymidine kinase) gene. The 3×FLAG gene segment was inserted in-frame to be expressed at the carboxyl terminus of the gD. The locations of other relevant genes are shown (UL24: nuclear protein).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

HSV-1, Herpes Simplex Virus-1; EHV-1, Equine Herpes virus-1; MHC, major histocompatibility complex; 3×FLAG peptide: DYKDHDGDYKDHDIDYKDDDDK (SEQ ID NO: 16); FACS, fluorescence-activated cell sorting; gD, glycoprotein D; IgG, immunoglobulin G; IFN, interferon; TNF, tissue necrosis factor; pfu, plaque-forming units; FITC, Fluorescein isothiocyanate; PBS, phosphate-buffered saline; HE, hematoxylin-eosin.

Definitions

The term "adjuvant molecule" as used herein refers to surface proteins capable of eliciting an immune response in a host. In particular embodiments, the adjuvant molecule is a "membrane-anchored form" of the adjuvant molecule which indicates that the adjuvant molecule has been engineered to include a signal peptide (SP) and a membrane anchor sequence to direct the transport and membrane orientation of the protein. Thus, in embodiments, a membrane-anchored form of an adjuvant molecule is a recombinant protein including a portion of a protein fused to a SP and membrane anchor sequence.

The term "administration" as used herein refers to introducing a composition (e.g., a vaccine, adjuvant, or immunogenic composition) of the present disclosure into a subject. The preferred route of administration of the vaccine composition is intravenous. However, any route of administration, such as oral, topical, subcutaneous, peritoneal, intra-arterial, inhalation, vaginal, rectal, nasal, introduction into the cerebrospinal fluid, or instillation into body compartments, can be used.

The term "antibody" as used herein refers to an immunoglobulin which specifically binds to and is thereby defined as complementary with a particular spatial and polar organization of another molecule. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and $F(ab')_2$, Fab', scFv, and the like. In addition, aggregates, polymers, and conjugates of immunoglobulins or their fragments can be used where appropriate so long as binding affinity for a particular molecule is maintained.

The term "antigen" as used herein refers to a molecule with one or more epitopes that stimulate a host's immune system to make a secretory, humoral and/or cellular antigen-specific response, or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof. For use with the compositions of the present disclosure, one or more antigens (native protein or protein fragment), may be provided directly or as part of a recombinant nucleic acid expression system to provide an antigenic product to trigger a host immune response. The term "antigen" as used herein can further refer to any entity that binds to an antibody disposed on an antibody array and induces at least one shared conformational epitope on the antibody. Antigens can be proteins, peptides, antibodies, small molecules, lipid, carbohydrates, nucleic acid, and allergens. An antigen may be in its pure form or in a sample in which the antigen is mixed with other components.

The terms "antigen-binding site" or "binding portion" as used herein refer to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

The term "antigenic component" as used herein refers to a component derived from an organism capable of stimulating an immune response in an animal, preferably a mammal including mouse and human. An antigenic component may be an immunogenic agent. The antigenic component may comprise sub-cellular components including, organelles, membranes, proteins, lipids, glycoproteins and other components derived from the organism. The antigenic component may be derived from a whole organism, for example a whole parasite, or a part of an organism, for example a cell or tissue of an organism. Also, a sub-set of proteins may be purified, for example by size fractionation or affinity purification, and recombined.

The term "coding sequence" as used herein refers to a sequence which "encodes" a selected polypeptide and is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

The term "contacting a cell or population of cells" as used herein refers to delivering a probe according to the present disclosure to an isolated or cultured cell or population of cells, or administering the probe in a suitable pharmaceutically acceptable carrier to the target tissue of an animal or human. Administration may be, but is not limited to, intravenous delivery, intraperitoneal delivery, intramuscularly, subcutaneously, or by any other method known in the art. One advantageous method is to deliver directly into a blood vessel leading into a target organ or tissue such as a prostate, and so reducing dilution of the probe in the general circulatory system.

The term "epitope" as used herein refers to the site on an antigen that is recognized by a T-cell receptor and/or an antibody.

The terms "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "expression vector" as used herein refers to a nucleic acid useful for expressing the DNA encoding the protein used herein and for producing the protein. The expression vector is not limited as long as it expresses the gene encoding the protein in various prokaryotic and/or eukaryotic host cells and produces this protein. When yeast, animal cells, or insect cells are used as hosts, an expression vector preferably comprises, at least, a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used.

A promoter/operator region to express the protein in bacteria comprises a promoter, an operator, and a Shine-Dalgarno (SD) sequence (for example, AAGG). For example, when the host is *Escherichia*, it preferably comprises Trp promoter, lac promoter, recA promoter, lambda.PL promoter, b 1pp promoter, tac promoter, or the like. When the host is a eukaryotic cell such as a mammalian cell, examples thereof are SV40-derived promoter, retrovirus promoter, heat shock promoter, and so on. As a matter of course, the promoter is not limited to the above examples. In addition, using an enhancer is effective for expression. A preferable initiation codon is, for example, a methionine codon (ATG). A commonly used termination codon (for example, TAG, TAA, and TGA) is exemplified as a termination codon. Usually, used natural or synthetic terminators are used as a terminator region. An enhancer sequence, polyadenylation site, and splicing junction that are usually used in the art, such as those derived from SV40, can also be used. A selectable marker usually employed can be used according to the usual method. Examples thereof are resistance genes for antibiotics, such as tetracycline, ampicillin, or kanamycin.

The expression vector used herein can be prepared by continuously and circularly linking at least the above-mentioned promoter, initiation codon, DNA encoding the protein, termination codon, and terminator region to an appropriate replicon. If desired, appropriate DNA fragments (for example, linkers, restriction sites, and so on) can be used by a method such as digestion with a restriction enzyme or ligation with T4 DNA ligase. Transformants can be prepared by introducing the expression vector mentioned above into host cells.

The term "immunogenic composition" as used herein are those which result in specific antibody production or in cellular immunity when injected into a host.

The immunogenic compositions and/or vaccines of the present disclosure may be formulated by any of the methods known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active immunogenic ingredients are often mixed with excipients or carriers, which are pharmaceutically acceptable and compatible with the active ingredient. Suitable excipients include but are not limited to, water, saline, dextrose, glycerol, ethanol, or the like and combinations thereof. The concentration of the immunogenic polypeptide in injectable, aerosol or nasal formulations is usually in the range of about 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or other agents, which enhance the effectiveness of the vaccine. Examples of agents which may be effective include, but are not limited to, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of the auxiliary substances may be determined by measuring the amount of antibodies (especially IgG, IgM or IgA) directed against the immunogen resulting from administration of the immunogen in vaccines which comprise the adjuvant in question. Additional formulations and modes of administration may also be used.

The immunogenic compositions and/or vaccines of the present disclosure can be administered in a manner compatible with the dosage formulation and in such amount and manner as will be prophylactically and/or therapeutically effective, according to what is known to the art. The quantity to be administered, which is generally in the range of about 1 to 1,000 micrograms of protein per dose and/or adjuvant molecule per dose, more generally in the range of about 5 to 500 micrograms of glycoprotein per dose and/or adjuvant molecule per dose, depends on the nature of the antigen and/or adjuvant molecule, subject to be treated, the capacity of the host's immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or immunogenic composition may be given in a single dose; two-dose schedule, for example, two to eight weeks apart; or a multi-dose schedule. A multi-dose schedule is one in which a primary course of vaccination may include 1 to 10 or more separate doses, followed by other doses administered at subsequent time intervals as required to maintain and/or reinforce the immune response (e.g., at 1 to 4 months for a second dose, and if needed, a subsequent dose(s) after several months). Humans (or other animals) immunized with the virosomes of the present disclosure are protected from infection by the cognate virus.

It should also be noted that the vaccine or immunogenic composition can be used to boost the immunization of a host having been previously treated with a different vaccine such as, but not limited to, DNA vaccine and a recombinant virus vaccine.

The term "immunogenic fragment" as used herein refers to a fragment of an immunogen that includes one or more epitopes and thus can modulate an immune response or can act as an adjuvant for a co-administered antigen. Such fragments can be identified using any number of epitope mapping techniques, well known in the art (see, e.g., Epitope Mapping Protocols in Methods in Molecular Biology, Vol. 66 (Morris, G. E., Ed., 1996) Humana Press, Totowa, N.J.).

Immunogenic fragments can be at least about 2 amino acids in length, more preferably about 5 amino acids in length, and most preferably at least about 10 to about 15 amino acids in length. There is no critical upper limit to the length of the fragment, which can comprise nearly the full-length of the protein sequence or even a fusion protein comprising two or more epitopes.

The term "immunoglobulin" as used herein refers to a class of proteins that exhibit antibody activity and bind to other molecules (e.g., antigens and certain cell-surface receptors) with a high degree of specificity. Immunoglobulins can be divided into five classes: IgM, IgG, IgA, IgD, and IgE. IgG is the most abundant antibody class in the body and assumes a twisted "Y" shape configuration. With the exception of the IgMs, immunoglobulins are composed of four peptide chains that are linked by intrachain and interchain disulfide bonds. IgGs are composed of two polypeptide heavy chains (H chains) and two polypeptide light chains (L chains) that are coupled by non-covalent disulfide bonds.

The light and heavy chains of immunoglobulin molecules are composed of constant regions and variable regions. For example, the light chains of an IgG1 molecule each contain a variable domain ($V_L$) and a constant domain ($C_L$). The heavy chains each have four domains: an amino terminal variable domain ($V_H$), followed by three constant domains ($C_H$1, $C_H$2, and the carboxy terminal $C_H$3). A hinge region corresponds to a flexible junction between the $C_H$1 and C $C_H$2 domains. Papain digestion of an intact IgG molecule results in proteolytic cleavage at the hinge and produces an Fc fragment that contains the $C_H$2 and $C_H$3 domains, as well as two identical Fab fragments that each contain a $C_H$1 $C_L$, $V_H$, and $V_L$ domain. The Fc fragment has complement- and tissue-binding activity. The Fab fragments have antigen-binding activity Immunoglobulin molecules can interact with other polypeptides through a cleft within the $C_H$2-$C_H$3 domain. This "$C_H$2-$C_H$3 cleft" typically includes the amino acids at positions 251-255 within the $C_H$2 domain and the amino acids at positions 424-436 within the $C_H$3 domain. As used herein, numbering is with respect to an intact IgG molecule as in Kabat et al. (Sequences of Proteins of Immunological Interest, 5th ed., Public Health Service, U.S. Department of Health and Human Services, Bethesda, Md.). The corresponding amino acids in other immunoglobulin classes can be readily determined by those of ordinary skill in the art.

The Fc region can bind to a number of effector molecules and other proteins, including the cellular Fe Receptor that provides a link between the humoral immune response and cell-mediated effector systems (Hamano et al., (2000) *J. Immunol.* 164: 6113-6119; Coxon et al., (2001) *Immunity* 14: 693-704; Fossati et al., (2001) *Eur. J. Clin. Invest.* 31: 821-831). The Fcγ receptors are specific for IgG molecules, and include FcγRI, FcγRIIa, FcγRIIb, and FcγRIII. These isotypes bind with differing affinities to monomeric and immune-complexed IgG.

The term "immunological response" as used herein refers to the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells.

One aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The term "gene controlling regions" as used herein refers to, but is not limited to, transcription promoters, transcription enhancer elements, transcription termination signals, polyadenylation sequences (located 3' to the translation stop codon), sequences for optimization of initiation of translation (located 5' to the coding sequence), and translation termination sequences, see e.g., McCaughan et al., (1995) *Proc. Natl. Acad. Sci. U.S.A.* 92: 5431-5435; Kochetov et al., (1998) *FEBS Letts.* 440: 351-355.

The term "immunization" as used herein refers to the process of inducing a continuing protective level of antibody and/or cellular immune response which is directed against an antigen, either before or after exposure of the host to the antigen.

The term "immunogenic amount" as used herein refers to an amount capable of eliciting the production of antibodies directed against the virus in the host to which the vaccine has been administered.

The term "immunogenic carrier" as used herein refers to a composition enhancing the immunogenicity of the virosomes from any of the viruses discussed herein. Such carriers include, but are not limited to, proteins and polysaccharides, and microspheres formulated using, for example, a biodegradable polymer such as DL-lactide-co-glycolide, liposomes, and bacterial cells and membranes. Protein carriers may be joined to the proteinases, or peptides derived therefrom, to form fusion proteins by recombinant or synthetic techniques or by chemical coupling. Useful carriers and ways of coupling such carriers to polypeptide antigens are known in the art.

The term "immunogenic composition" as used herein refers to a composition that comprises an antigenic molecule where administration of the composition to a subject results in the development in the subject of a humoral and/or a cellular immune response to the antigenic molecule of interest.

The term "immunological response" as used herein refers to a composition or vaccine that includes an antigen and that triggers in the host a cellular- and/or antibody-mediated immune response to antigens. Usually, such a response may include antibody production (e.g., in the intestinal tract, from germinal centers in lymph nodes, etc.), B cell proliferation, helper T cells, cytotoxic T cell proliferation, Natural Killer activation specifically to the antigen or antigens and/or fluids, secretions, tissues, cells or hosts infected therewith.

The term "immunopotentiator," as used herein, is intended to mean a substance that, when mixed with an immunogen, elicits a greater immune response than the immunogen alone. For example, an immunopotentiator can enhance immunogenicity and provide a superior immune response. An immunopotentiator can act, for example, by enhancing the expression of co-stimulators on macrophages and other antigen-presenting cells.

The term "nucleic acid molecule" as used herein refers to DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. An "isolated" nucleic acid molecule is one that is separated from other nucleic acid molecules that are present in the natural source of the nucleic acid. A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

The terms "nucleic acid," "nucleic acid sequence," or "oligonucleotide" also encompass a polynucleotide. A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which natural nucleotides have been partially replaced with modified nucleotides.

The term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

The term "operably linked" as used herein refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The terms "pharmaceutically acceptable" or "pharmacologically acceptable" as used herein refer to a material that is not biologically or otherwise undesirable, i.e., the material may be administered to an individual in a formulation or composition without causing any undesirable biological effects or interacting in a deleterious manner with any of the components of the composition in which it is contained.

The term "Polymerase Chain Reaction" or "PCR" as used herein refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569,672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

The term "polypeptide" as used herein refers to proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allothreonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

The term "primer" as used herein refers to an oligonucleotide complementary to a DNA segment to be amplified or replicated. Typically primers are used in PCR. A primer hybridizes with (or "anneals" to) the template DNA and is used by the polymerase enzyme as the starting point for the replication/amplification process. By "complementary" it is meant that the primer sequence can form a stable hydrogen bond complex with the template.

The term "recombinant" as used herein refers to a polynucleotide of genomic, cDNA, semisynthetic, or synthetic origin which, by virtue of its origin or manipulation (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting eukaryotic cell lines cultured as unicellular entities, are used interchangeably and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition and are covered by the above terms. Techniques for determining amino acid sequence "similarity" are well known in the art.

The term "region" as used herein refers interchangeably with "domain" and refers to a functional unit of a peptide sequence.

The term "therapeutically effective amount" relates to the amount or dose of an active compound of the disclosure or composition comprising the same, that will lead to one or more desired effects, in particular, one or more therapeutic effects or beneficial pharmacokinetic profiles. A therapeutically effective amount of a substance can vary according to factors such as the disease state, age, sex, and weight of the subject, and the ability of the substance to elicit a desired response in the subject. A dosage regimen may be adjusted to provide the optimum therapeutic response or pharmacokinetic profile. For example, several divided doses may be administered daily or the dose may be proportionally reduced as indicated by the exigencies of the therapeutic situation.

A "vaccine" is capable of providing protective immunity against an organism. The vaccine may provide protection against a same (i.e. homologous) or different (i.e. heterologous) strain of an organism. The vaccine of the invention preferably is capable of providing protection against homologous and heterologous species, variants or strains.

The term "vector" as used herein refers to a genetic unit (or replicon) to which or into which other DNA segments can be incorporated to effect replication, and optionally, expression of the attached segment.

The terms "heterologous polypeptide sequence" or a "heterologous nucleic acid" as used herein refer to an amino acid or nucleotide sequence that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA.

DESCRIPTION

The present disclosure encompasses the construction and testing of an effective HSV-1-vectored vaccine designed to prevent EHV-1 infections. The HSV-1 VC2 strain of the disclosure contains the gK Δ31-68 deletion and a deletion of the amino-terminal 19 amino acids of UL20, which render the virus unable to enter into distal axons of ganglionic neurons, while the virus replicates efficiently in epithelial and fibroblast cells and generates robust and protective immune responses in mice (Stanfield et al., (2014) *PLoS One* 9:e109890) and guinea pigs.

The mouse model of EHV-1 infection has been used to investigate the vaccine potential of various EHV-1 immunogens, the effect of antiviral agents on EHV-1 infection, and the pathogenicity of EHV-1 strain variants and deletion or insertional mutants (Walker et al., (1999) *Vet. Microbiol* 68: 3-13; Frampton et al., (2004) *Virus Genes* 29: 9-17; Ma et al., (2012) *PLoS One* 7:e34425). The lung histopathology in EHV-1-infected mice is similar to that of infected horse, and is characterized by an acute necrotizing alveolitis and bronchiolitis, eosinophilic intranuclear inclusion bodies in bronchiolar epithelial cells (Bartels et al., (1998) *Xenobiotica* 28: 579-594; Bartels et al., (1998) *Immunology* 93: 329-334). Although the mouse model of EHV-1 infection is not ideal, its extensive use has contributed toward the development of vaccine strategies. The live-attenuated HSV-1 VC2 vaccine strain expressing the EHV-1 gD can efficiently infect equine cells and generates strong and protective anti-EHV-1 immune responses in mice that may also protect horses against EHV-1 infection.

The present disclosure, therefore, encompasses embodiments of recombinant viral vectors comprising a nucleotide sequence encoding a live-attenuated Herpes Simplex Virus Type-1 (HSV-1) VC2 vaccine strain and a nucleotide sequence encoding a heterologous polypeptide operably linked to a promoter.

In particular, the disclosure encompasses embodiments of a recombinant viral vector, wherein the nucleotide sequence encoding a heterologous polypeptide is operably linked to a promoter and encodes the glycoprotein D (gD) of Equine Herpesvirus-1 (EHV-1) or an immunogenic fragment thereof.

The present disclosure further encompasses embodiments of methods of generating an antibody or an immune response in an animal, the methods comprising the step of administering to an animal a pharmaceutically acceptable composition comprising a recombinant viral vector, said vector comprising a nucleotide sequence encoding a live-attenuated Herpes Simplex Virus Type-1 (HSV-1) VC2 vaccine strain and a nucleotide sequence encoding a heterologous polypeptide operably linked to a promoter. It is further contemplated that a nucleotide sequence encoding an immunogenic peptide or polypeptide not derived from the glycoprotein D (gD) of Equine Herpesvirus-1 (EHV-1) may be operably linked to a promoter or gene expression controlling region for expression from the recombinant viral vectors of the disclosure.

Vaccination remains the best option to combat EHV-1 infection and several different strategies of vaccination have been investigated and developed over the past decades. It is now shown that the live-attenuated Herpes Simplex Virus Type-1 (HSV-1) VC2 vaccine strain, which has been shown to be unable to enter into neurons and establish latency in mice, can be utilized as a vector for the heterologous expression of the Equine Herpesvirus-1 (EHV-1) glycoprotein D (gD), and that intramuscular immunization of mice resulted in strong anti-viral humoral and cellular immune responses.

The VC2-EHV-1-gD recombinant virus was constructed by inserting an EHV-1 gD expression cassette under the CMV immediate early promoter control into the VC2 vector in place of the HSV-1 thymidine kinase (UL23) gene. The vaccines were introduced into mice through intramuscular injection. Both VC2-EHV-1-gD and the Vetera commercially available vaccine produced neutralizing antibody, which was significantly higher in comparison to VC2 and mock-vaccinated animals ($p<0.01$ or $p<0.001$). Analysis of EHV-1-reactive IgG subtypes demonstrated that vaccination with the VC2-EHV-1-gD vaccine stimulated robust IgG1 and IgG2a antibodies after three vaccinations ($p<0.001$). Vetera vaccinated mice produced significantly higher IgM than other groups before and after challenge ($p<0.01$ or $P<0.05$). Vaccination with VC2-EHV-1-gD stimulated strong cellular immune responses characterized by upregulation of both interferon and TNF positive $CD4^+$ T and $CD8^+$ T cells. Overall, the data suggest that the HSV-1 VC2 vaccine strain can be used as a viral vector for vaccination of horses, as well as potentially for other economically important animals.

A novel virus-vectored VC2-EHV-1-gD vaccine was constructed using the live-attenuated HSV-1 VC2 vaccine strain. This vaccine stimulated strong humoral and cellular immune responses in mice suggesting that it could protect horses against EHV-1 infection.

For the first time the use of the human herpes simplex virus type-1 (HSV-1) VC2 vaccine strain, as a potential live virus vaccine to combat EHV-1 infections. The VC2 virus was engineered to express the EHV-1 gD glycoprotein and shown to elicit protective humoral and cellular immune responses in mice. The work indicates that the human HSV-1 VC2 vaccine strain can be used as a vector for the production of heterologous vaccines expressing immunogens that can protect horses and other animals against economically important pathogens.

The VC2 vaccinated group generated anti-EHV-1 neutralizing activity against EHV-1 infection suggesting the presence of common immunogenic determinants between HSV-1 and EHV-1. HSV-1 and EHV-1 share a number of conserved genes and overall genomic arrangement characteristic of the alphaherpesviruses subfamily. However, individual homologous viral proteins differ substantially in their primary sequences. Specifically, HSV-1 and EHV-1 gDs exhibit 19.2% identity and 31.5% similarity. However, alignment of HSV-1 gD sequences indicates conservation of a certain continuous amino acid segments that could provide shared immunogenic responses. In addition, based on the overall structure conservation of EHV-1 and HSV-1 gDs (Wellington et al., (1996) *Arch. Virol.* 141: 1785-1793; Flowers & O'Callaghan (1992) *J. Virol.* 66: 6451-6460), certain conformational epitopes may be conserved and contributing to the observed cross-neutralizing activity of VC2. Also, it is likely that a number of other viral proteins may contribute strain common immunogenic determinants that produce cross-neutralizing activity.

Figure 5:
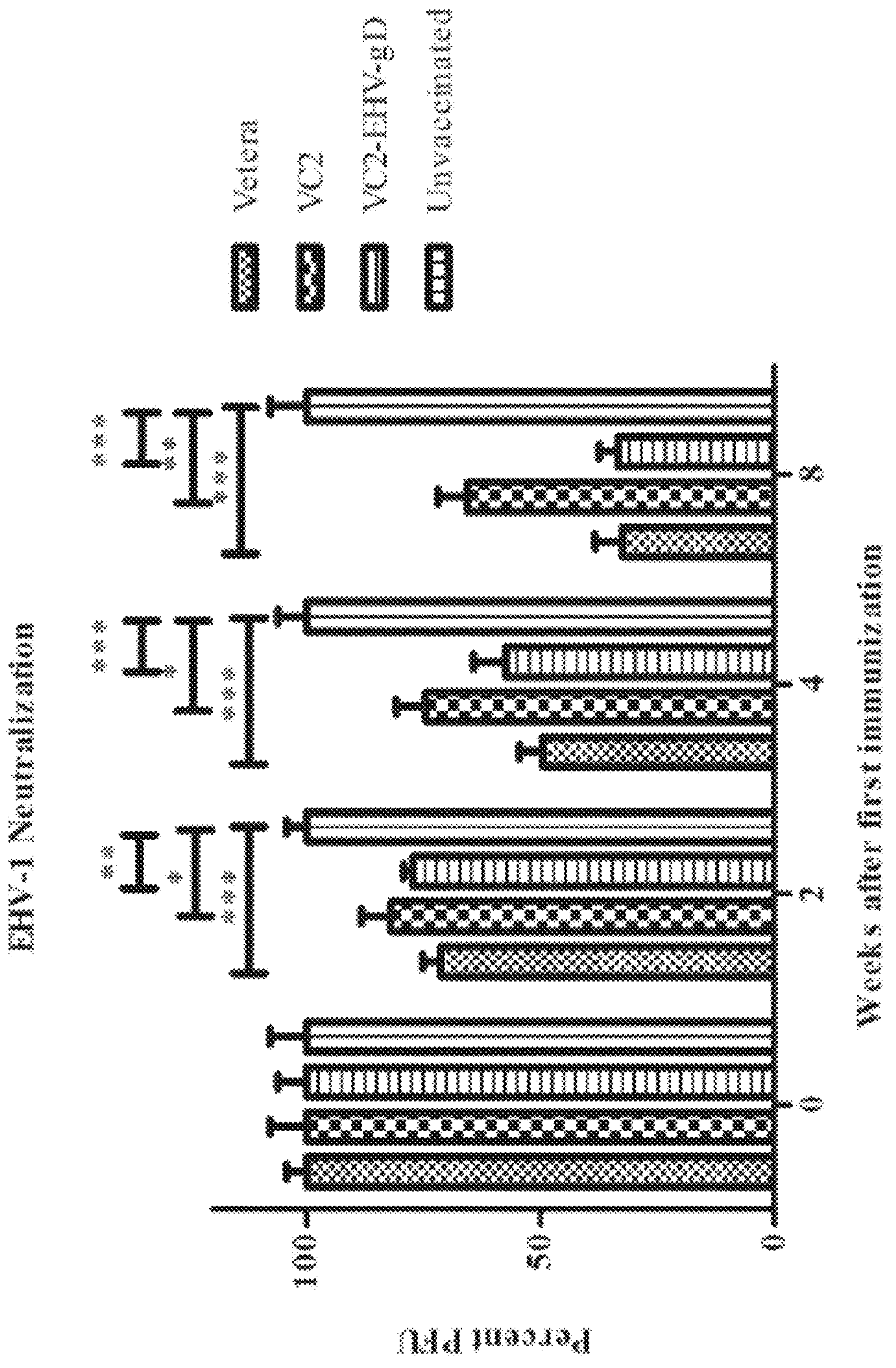
FIG. 5 is a graph illustrating virus neutralization activities. All sera were diluted 1:20 in growth medium and tested for ability to neutralize approximately 100 PFU of EHV-1. Data were statistically analyzed by one-way ANOVA followed by Newman-Keuls Multiple Comparison Test (*$p<0.05$, $p<0.01$, *$p<0.001$).
Figure 6B:
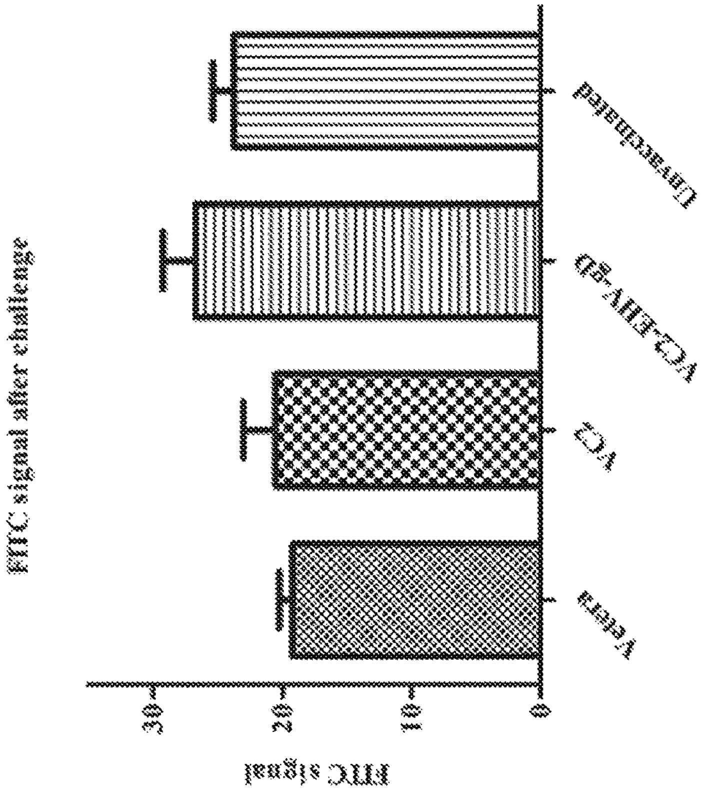
FIG. 6B is a graph illustrating anti-EHV-1 activities reaction. Mouse sera from the Vetera, VC2, VC2-EHV-1-gD and unvaccinated mice groups after challenge were diluted 1:20 in growth medium and tested for their ability to react with EHV-1 infected RB13 cells. FACS data were analyzed by one-way ANOVA followed by Newman-Keuls Multiple Comparison Test (*$p<0.05$, $p<0.01$, *$p<0.001$).
Figure 6A:
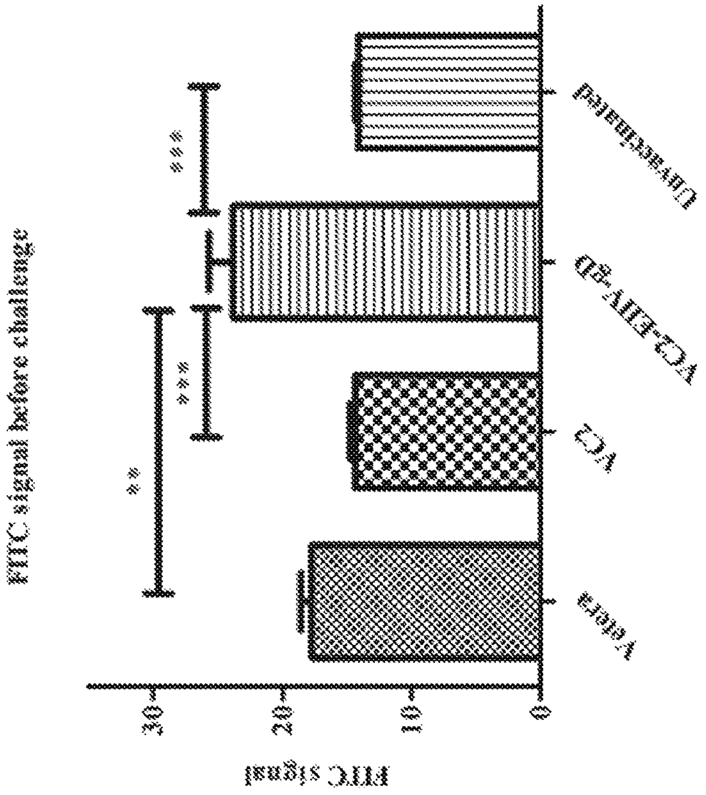
FIG. 6A is a graph illustrating anti-EHV-1 activities reaction. Mouse sera from the Vetera, VC2, VC2-EHV-1-gD and unvaccinated mice groups before challenge were diluted 1:20 in growth medium and tested for their ability to react with EHV-1 infected RB13 cells. FACS data were analyzed by one-way ANOVA followed by Newman-Keuls Multiple Comparison Test (*$p<0.05$, $p<0.01$, *$p<0.001$).

The VC2-EHV-1-gD virus stimulated strong virus-neutralizing activity in comparison to both unvaccinated and VC2 vaccinated animals, which was similar to that generated by the commercial EHV-1 killed virus vaccine. It has been reported that intranasal or intramuscular immunization with EHV-1 gD produces antigen-specific IgG responses (Fuentealba et al., (2014) *J. Virol. Methods* 202: 15-18; Fuentealba et al., (2014) *J. Comp. Pathol* 151: 384-393; Weerasinghe et al., (2006) *Vet. Immunol. Immunopathol.* 111: 59-66; Foote et al., (2005) *Vet. Immunol. Immunopathol.* 105: 47-57; Ruitenberg et al., (2001) *Virus Res.* 79: 125-135, Flowers & O'Callaghan (1992) *J. Virol.* 66: 6451-6460; Ruitenberg et al., (2000) *Vet. Microbiol.* 76: 117-127; Ruitenberg et al., (1999) *Vaccine* 17: 237-244; Love et al., (1992) *Vet. Microbiol.* 30: 387-394). In addition, the presence of virus neutralizing (VN) antibody prior to EHV-1 infection was shown to be associated with a reduction in the amount and duration of nasopharyngeal virus shedding (Kydd et al., (2003) *Vet. Immunol. Immunopathol.* 96: 207-217; Hannant et al., (1993) *Res. Vet. Sci.* 54: 299-305). Flow cytometry tests revealed that VC2-EHV-1-gD virus stimulated significantly higher specific anti-EHV-1 antibody than the commercial vaccine suggesting that this response plays a major role in conferring protection against EHV-1 infection (FIGS. 6A and 6B, $p<0.001$). IgM antibodies are highly cross-reactive antibodies, which are typically produced early after an infection and replaced later by higher affinity IgG antibodies through isotype switching (Bego et al., (2008) *J. Virol. Methods* 151: 204-210). Mice in the Vetera vaccinated group produced significantly higher anti-EHV-1 IgM level than other groups before and after challenge (FIG. 9, $p<0.05$ or $p<0.01$), which may have contributed to the observed virus neutralizing activities (FIG. 5). However, the Vetera vaccine produced significantly lower anti-EHV-1 IgG than the VC2-EHV-1-gD vaccine (FIGS. 6A and 6B, $p<0.01$). The IgG2a and IgG1 immunoglobulin isotypes are markers for Th1 and Th2 responses respectively (Song et al., (2014)

*Zhonghua Kou Qiang Yi Xue Za Zhi* 49: 89-94; Ebrahimpoor et al., (2013) *Iran. J. Allergy Asthma Immunol.* 12: 361-367; Koyama & Ito (2001) *Parasitol. Res.* 87: 570-572; Berger A. (2000) BMJ 321: 424).

The IgG subclass induced after immunization or challenge is an indirect measure of the relative contribution of Th2-type cytokines versus Th1-type cytokines. The production of IgG1-type antibodies is primarily induced by Th2-type cytokines, whereas production of IgG2a-type antibodies reflects the involvement of Th1-type cytokines (Yadav & Khuller (2001) *Immunol. Cell Biol.* 79: 207-212). These IgG subtypes were investigated in mice before and after EHV-1 challenge. The VC2-EHV-1-gD vaccinated mice generated high IgG1 and IgG2a responses before challenge. However, IgG2a levels were enhanced after challenge, indicating a natural IgG2a response to EHV-1 infection. In comparison, mice in other groups developed lower levels of IgG1 and IgG2a (FIG. 9). These results indicate that the VC2-EHV-1-gD vaccination generated a strong Th1 response priming the animals prior to challenge. Cytotoxic T lymphocytes (CTL) are thought to be the primarily responsible for eliminating EHV-1 infected cells (Soboll et al., (2003) *J. Gen. Virol.* 84: 2625-2634; Allen et al., (2004) *Infection Dis. Livestock* 76: 829-859; Allen et al., (2008) *Equine Vet. J.* 40: 105-110; Allen et al., (1995) *J. Virol.* 69: 606-612). The VC2-EHV-1-gD vaccine increased the numbers of IFN-γ producing CD8+ cells after stimulation of peptide 3 indicating elicitation of anti-EHV-1 gD $CD8T^+$ cell responses (FIGS. 10A-10D). IFN-γ is commonly produced by effector $CD8^+$ T lymphocytes and upon recognition of the specific antigen, CTL activity can be measured (O'Flaherty et al., (2015) *PLoS One* 10:e0135719; McCarthy et al., (2015) *J. Virol.* 89: 468-479). Several studies conducted in mice have demonstrated an important role for IFN-γ in immune protection from herpesvirus infections (Mikloska & Cunningham (2001) *J. Virol.* 75: 11821-11826; Cantin et al., (1999) *J. Virol.* 73: 3418-3423). Also, IFN-γ is critical for innate and adaptive immunity against viral infections in general and is an important activator of macrophages and inducer of MHC molecule expression, while virus-specific $CD8^+$ T cells are thought to produce long-lived protection (Shin & Iwasaki (2012) *Nature* 491: 463-467).

Equine PBMC induced IFN-γ production by a significantly higher percentage among post-EHV-1 infection compared to pre-infection samples after in vitro stimulation with EHV-1 gD peptides. This response was associated with an increase in virus-specific CTL activity, a critical immune effector for the control of EHV-1 infection and disease (Breathnach (2005) *Vet. Immunol. Immunopathol.* 103:207-215). Therefore, the observed $CD8^+$ T cell response generated by the VC2-EHV-1-gD vaccine must be a strong contributing factor in limiting the EHV-1 infection in mice. It remains to be tested whether similar immune responses can be generated in horses. Tumor necrosis factor (TNF or TNF-α) is an important cytokine that triggers local containment of infections. The VC2-EHV-1-gD vaccine group generated more TNF producing $CD8^+$ T cells post challenge comparing to other groups, which was in agreement with a previous report that showed a concurrent upregulation of TNF transcripts post infection in EHV-1 strain RacL11-infected mice (Smith et al., (2000) *J. Virol.* 74: 10034-10040). TNF stimulates endothelial cells to express proteins that trigger blood clotting in the local small vessels, occluding them and cutting off blood flow. This physiological effect may prevent the viruses from entering the bloodstream and spreading through the blood to organs all over the body resulting in reduction of EHV-1 viremia. Further studies are needed to determine the specific role that TNF may play in the pathogenesis of EHV-1 infection.

Recently, the U.S. Food and Drug Administration (FDA) approved a genetically modified HSV-1 oncolytic viral therapy for the local treatment of unresectable cutaneous, subcutaneous and nodal lesions in patients with recurrent melanoma after initial surgery. The HSV-1 VC2 strain has been shown to elicit robust humoral and cellular immune responses in mice, non-human primates and guinea pigs and to confer protection against HSV-2 challenge in mice (Stanfield et al., (2014) *PLoS One* 9:e109890), non-human primates (Stanfield et al., (2017) *Vaccine* 35: 536-543), and guinea pigs (Stanfield et al, manuscript submitted). Here, we describe the use of the VC2 virus for the production of a modified-live attenuated vaccine against EHV-1. It remains to be tested whether VC2 is safe for the use of horses and other animals, which will pave the way for its use for the production of viral vector vaccines against major pathogens of economically important animal species.

The present disclosure provides for a vaccine comprising an HSV-EHV recombinant viral vector of the disclosure and a pharmaceutically acceptable carrier or diluent.

A live attenuated recombinant viral vector according to the present disclosure can be used to vaccinate equines, particularly domestic and non-domestic, and more specifically horses. Vaccination with such a live vaccine is preferably followed by replication of the virus within the inoculated host, which host will then elicit an immune response against EHV, and the animal inoculated with the HSV recombinant according to the disclosure will be immune to infection by EHV.

For the preparation of a live vaccine, the recombinant EHV mutant according to the present disclosure can be grown on a cell culture, for example, of equine, rabbit, hamster or calf origin. The viruses thus grown can be harvested by collecting the tissue cell culture fluids and/or cells. The live vaccine may be prepared in the form of a suspension or may be lyophilized. The vaccine according to the disclosure can be prepared using standard techniques available in the art. In general, the vaccine is prepared by mixing the virus with a pharmaceutically acceptable carrier or diluent.

For administration to animals, the EHV mutant according to the present disclosure can be given, inter alia, intranasally, intradermally, subcutaneously or, most advantageously intramuscularly.

Pharmaceutically acceptable carriers or diluents that can be used to formulate a vaccine according to the disclosure are sterile and physiologically compatible such as, for example, sterile water, saline, aqueous buffers such as alkali metal phosphates (e.g. PBS), alcohols, polyols and the like. In addition, the vaccine according to the disclosure may comprise other additives such as adjuvants, stabilizers, anti-oxidants, preservatives and the like. Suitable adjuvants include, but are not limited to, aluminum salts or gels, carbomers, non-ionic block copolymers, tocopherols, monophosphoryl lipid A, muramyl dipeptide, oil emulsions (w/o or o/w), and cytokines. The amount of adjuvant added depends on the nature of the adjuvant.

Suitable stabilizers for use in a vaccine according to the disclosure are, for example, carbohydrates including sorbitol, mannitol, starch, sucrose, dextrin and glucose, proteins such as albumin or casein, and buffers like alkaline phosphates. Suitable preservatives include, amongst others, thimerosal, merthiolate and gentamicin.

Live vaccines according to the disclosure comprise an effective amount of the afore-mentioned HSV mutant virus and a pharmaceutically acceptable carrier. The term "effective" as used herein is defined as the amount sufficient to induce an immune response in the target animal. The amount of virus will depend on the route of administration and the time of administration, as well as age, general health and diet of the subject to be vaccinated.

The dosages in which the live vaccines according to the disclosure can prevent infectious disease can be readily determined by routine trials with appropriate controls and are well within the routine skills of the practitioner.

The useful dosage to be administered will vary depending on the age, weight, mode of administration and type of pathogen against which vaccination is sought. A suitable dosage can be, for example, about $10^3$-$10^7$ pfu/animal.

According to a further aspect thereof, the disclosure provides a process for the preparation of the recombinant viral viruses and vectors of the disclosure, comprising transfecting a cell culture with a recombinant DNA molecule and HSV genomic DNA.

One aspect of the present disclosure encompasses embodiments of a recombinant nucleic acid comprising a nucleotide sequence encoding a live-attenuated chimeric Herpes Simplex Virus Type-1 (HSV-1) VC2 virus and a nucleotide sequence encoding a heterologous polypeptide operably linked to a promoter.

In some embodiments of this aspect of the disclosure the nucleotide sequence encoding the heterologous polypeptide can be operably linked to a promoter encoding the glycoprotein D (gD) of Equine Herpesvirus-1 (EHV-1) or a fragment thereof.

Another aspect of the disclosure encompasses embodiments of a live-attenuated recombinant Herpes Simplex Virus Type-1 (HSV-1) VC2 virus comprising a nucleotide sequence encoding a nucleotide sequence encoding a heterologous polypeptide operably linked to a promoter.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

Still another aspect of the disclosure encompasses embodiments of a viral vaccine comprising a physiologically acceptable carrier and an immunogenic amount of a chimeric Herpes Simplex Virus Type-1 (HSV-1) VC2 virus comprising a nucleotide sequence encoding a heterologous polypeptide operably linked to a promoter.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

In some embodiments of this aspect of the disclosure the physiologically acceptable carrier can comprise an adjuvant.

Yet another aspect of the disclosure encompasses embodiments of a method of generating an antibody in an animal, wherein said method comprises the step of administering to an animal a pharmaceutically acceptable composition comprising a chimeric live-attenuated Herpes Simplex Virus Type-1 (HSV-1) VC2 virus, said virus comprising a nucleotide sequence encoding a heterologous polypeptide operably linked to a promoter a physiologically acceptable carrier.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

Still yet another aspect of the disclosure encompasses a method of generating an immune response in an animal, wherein said method comprising the step of administering to an animal a pharmaceutically acceptable composition comprising a chimeric live-attenuated Herpes Simplex Virus Type-1 (HSV-1) VC2 virus, said virus comprising a nucleotide sequence encoding a heterologous polypeptide operably linked to a promoter a physiologically acceptable carrier.

In some embodiments of this aspect of the disclosure the nucleotide sequence encoding the heterologous polypeptide operably linked to a promoter can encode the glycoprotein D (gD) of Equine Herpesvirus-1 (EHV-1) or a fragment thereof.

Numerical ranges recited herein by endpoints include all numbers and fractions subsumed within that range (e.g., 1 to 5 includes 1, 1 5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Further, it is to be understood that "a", "an," and "the" include plural referents unless the content clearly dictates otherwise. Thus, for example, reference to a composition comprising "a compound" includes a mixture of two or more compounds.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%)

within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Virus and Cells:

A clinical EHV-1 strain was isolated from the placenta of a thoroughbred horse in 2008. Vero (African green monkey kidney) and RK13 (Rabbit kidney) cells were cultured using DMEM with 5% FBS and 1% Primocin. NBL-6 (Equine dermal) cells were purchased from ATCC and cultured and maintained as instructed.

Construction of Recombinant Virus:

The construction and characterization of the HSV-1-VC2 virus has been described previously (Stanfield et al., (2014) *PLoS One* 9:e109890, incorporated herein by reference in its entirety). The VC2 genome cloned into a bacterial artificial chromosome (BAC) plasmid was utilized for the construction of the VC2-EHV-1-gD virus. The VC2 virus contains the gKΔ31-68 deletion as well as a deletion of the UL20 amino-terminal 19 amino acids (Stanfield et al., (2014) *PLoS One* 9:e109890).

VC2 is unable to enter into neuronal endings, while it produces protective humoral and cellular immunity that fully protected vaccinated mice against HSV lethal disease (Stanfield et al., (2014) *PLoS One* 9:e109890). The VC2-EHV-1-gD virus was constructed using the two-step red-mediated recombination system in *E. coli* SW105 cells, as described previously (Stanfield et al., (2014) *PLoS One* 9:e109890, Tischer et al., (2006) *Biotechniques* 40: 191-197). The EHV-1 gD sequence of 1206 bp was amplified by PCR using primers P1 (SEQ ID NO: 1) and P2 (SEQ ID NO: 2) (Table 1). The PCR products were digested with the restriction enzymes Not1 and BamH1 and inserted into the vector CMV-14 with a 3× FLAG epitope inserted in-frame at the carboxyl terminus of gD, resulting in recombinant plasmids CMV-gD. To construct CMV-gD-KanR, the KanR gene adjoining the I-Scel site was amplified by PCR from plasmid pEPkan-S using primers P3 (SEQ ID NO: 3) and P4 (SEQ ID NO: 4) (Table 1), digested with the restriction enzyme EcoR1 and inserted into CMV-gD (digested with EcoR1). The CMV-gD-KanR gene was amplified by PCR using primers P5 (SEQ ID NO: 5) and P6 (SEQ ID NO: 6) (Table 1) and then cloned into VC2 to replace UL23 (thymidine kinase). The kanamycin cassette was cleaved after expression of the I-Scel from plasmid pBAD-I-Scel. The inserted EHV-1 gD was verified by capillary DNA sequencing by using primers P7 to P12 (SEQ ID Nos: 7-12 (Table 1).

Synthetic Peptides:

BALB/c mouse MHC-1 and MHC-2 binding peptides were predicted by the IEDB T Cell Epitope Prediction Tools of the Immune Epitope Database and Analysis of the National Institutes of Health. The peptides were synthesized at the LSU Protein Core Lab (Table 2). These peptides (final concentration of ing in each reaction tube) were used to stimulate splenocytes from different vaccinated or challenged mice in vitro.

Vaccination:

Seven-week old female BALB/c mice were used in this study (60 mice total; 4 groups of 15 each). Each individual mouse was identified with an ear tag. Naïve animals did not get any vaccine, and the commercial vaccine Vetera® EHV$^{XP}$ 1/4 (Boehringer Ingelheim Vetmedica), an inactivated virus vaccine, was used to immunize a control group of animals. Vaccines were administered intramuscularly (cranial thigh muscles) in 2 week intervals for three times except for the naïve group (Table 3). Mice were observed and weighted daily over the course of the vaccination period. Blood/serum samples were collected from the facial vein every other week.

EHV-1 Respiratory Challenge in Mice:

Four groups of 11 mice were challenged intranasally with 20 μL containing $5\times10^7$ pfu wild type EHV-1 (10 μL per nostril) five weeks following the final administration of the vaccine. Mice were weighed daily over the course of this study and were monitored daily for the development of clinical signs such as ruffled fur, labored breathing, crouching or huddling behavior, sluggishness and loss of body weight. Previous research has demonstrated that body weight loss is an excellent indicator of EHV-1 infection in the mouse (van Woensel et al., (1995) *J. Virol. Methods* 54: 39-49). Three mice from each group were sacrificed after one week for tissue collection and histopathological analysis.

Tissue Collection and Analysis:

Four weeks after the third vaccination and one-week post challenge, three mice from each group were anesthetized by inhalation with 2-3% isoflurane. Maximum volume of blood was collected and mice were euthanized by cervical dislocation. Blood was allowed to clot at room temperature for at least 30 min. Serum was centrifuged, collected and stored at −20° C. until use. Spleens were excised from euthanized animals, minced and passed through a 10 mm nylon mesh cell strainer in RPMI 1460 with 10% heat-inactivated fetal bovine serum (HI-FBS). Cell suspensions were pelleted by centrifugation at 400×g for 7 min and cell concentration was adjusted to $10^7$ cells/ml for FACS analysis. The lung tissues from all four groups after challenge were collected and fixed in 10% formalin for immunohistochemistry.

Serum Neutralization:

Collected serum was used to neutralize 50 μL of approximately 100 PFU of EHV-1. After the sera were heated to 56° C. for 1 h to inactivate complement, samples were then diluted 1:10 in complete DMEM containing 10% heat inactivated FBS. Fifty microliters of virus were added to each dilution of serum to a total volume of 100 μL. The addition of the virus made final serum dilutions to 1:20. Serum virus mixtures were placed on a rocker at room temperature for 1 hour and titrated on NBL-6 cell monolayers.

FITC Flow Cytometry Analysis on Mice Sera:

RK13 cells were infected with EHV-1 and were disassociated by using 1 mM EDTA in PBS. Fixation/permeabilization solution was then added to the cells. Mouse sera (1:20) from different animal groups were mixed with the cells after two washes and incubated for 30 min at 37° C. Goat anti-mouse antibody conjugated with FITC was added to the suspension and incubated for another 30 min at 37° C. The cells were washed twice by adding 3 ml buffer (1% HI FBS in PBS). BD Fixative solution was applied to the cells and cells were kept at 4° C. till flow cytometry analysis.

Indirect Fluorescence Antibody (IFA) Analysis on Mice Sera:

Mouse sera (1:20) from different animal groups were placed on Equine Herpesvirus Type 1 IFA slides (catalog no. SLD-IFA-ERV, VMRD) and incubated for 30 min at 37° C. Anti-Equine IgG FITC Conjugate (catalog no. 043-10, VMRD) was added on the slides and incubated for another 30 min at 37° C. after wash. Slides were observed under Nikon fluorescence microscope.

Characterization of Antibody Subclass:

To determine the antigen specific antibody isotypes, 96-well plates were coated with 50 µl of EHV-1 infected cell lysate (20 µl/ml), then sera from each of the four groups of animals were diluted at 1:100 and tested in duplicate. To detect mouse IgG1, IgG2a, IgG2b, IgG3, IgA and IgM isotypes, anti-mouse IgG subclass-specific HRP-conjugated secondary antibodies (ABCAM®, 1/10000 dilution) were used.

Analysis of Immune Responses Using Polychromatic Flow Cytometry:

Spleens were excised from euthanized animals, minced and passed through a 10 mm nylon mesh cell strainer (Fisher Scientific) in RPMI 1640 medium containing 10% heat-inactivated fetal bovine serum (HI-FSB) and 1% Primocin. Cell suspensions were then pelleted by centrifugation at 400×g for 7 min at 4° C. Five milliliters of the ACK (Ammonium-Chloride-Potassium) Lysing Buffer was added to the cells. The cells were suspended and kept in room temperature for 7 min, and then the volumes were adjusted to a total of 25 ml with RPMI 1640 medium. The cell concentration was adjusted to $10^7$ cell/ml after washing with RPMI 1640 medium. Three different peptides (1 ng), 3 µl Golgi-Plus and 100 µl of $10^7$ cell/ml splenocyte suspension were gently mixed. Then the mixtures were incubated at 37° C. and the splenocytes were stimulated for 6 h. Cells were then stained with monoclonal rat anti-mouse CD3 antibody conjugated to PerCP-Cy® 5.5 (BD Biosciences), monoclonal rat anti-mouse CD4 antibody conjugated to PE (BD Biosciences), rat anti-mouse CD8a antibody conjugated to FITC (BD Biosciences), monoclonal rat anti-mouse IFN-γ antibody conjugated to APC (BD Biosciences) and rat anti-mouse TNF antibody conjugated to BV510 (BD Biosciences). FACS was assessed using an Accuri C6 personal flow cytometer. The data were analyzed using FlowJo software (v10.1r1, FlowJo Enterprise).

Immunohistochemistry Assay:

Lung tissue samples were fixed in 10% formalin, dehydrated through increasing ethanol gradients and paraffin embedded before obtaining 4-µm sections for hematoxylin and eosin (HE) staining and immunohistochemical assays. The EHV-1 glycoproteins G1 was detected using a rabbit anti-EHV-1 monoclonal murine antibody. The secondary antibody used was a goat anti-mouse IgG antibody (Abcam, U.S.). Finally, the slides were visualized using a light microscope (Nikon, Japan) and pictured using Olympus DP72 camera. Slides were analyzed and scored for cellular inflammation under light microscopy by a pathologist who was blind to the treatment groups, as previously described (Haeberle et al., (2001) *J. Virol.* 75: 878-890).

Briefly, inflammatory infiltrates were scored enumerating the layers of inflammatory cells surrounding the vessels and bronchioles. Zero to three layers of inflammatory cells was considered "normal." Moderate to abundant infiltrate (more than three layers of inflammatory cells surrounding 50% or more of the circumference of the vessel or bronchioles) was considered "abnormal." The number of abnormal perivascular and peribronchial spaces divided by the total perivascular and peribronchial spaces was the percentage reported as the pathology score. A total of up to 20 perivascular and peribronchial spaces per lung were randomly selected and counted for each animal. Similarly, immunohistochemical staining was scored by percentage of positive-stained bronchiolar cells and adjacent vascular endothelial cells. A total of approximately 70-100 bronchiolar epithelial cells and peribronchiolar vascular endothelial cells were counted for each lung tissue section.

Example 2

Figure 1B:
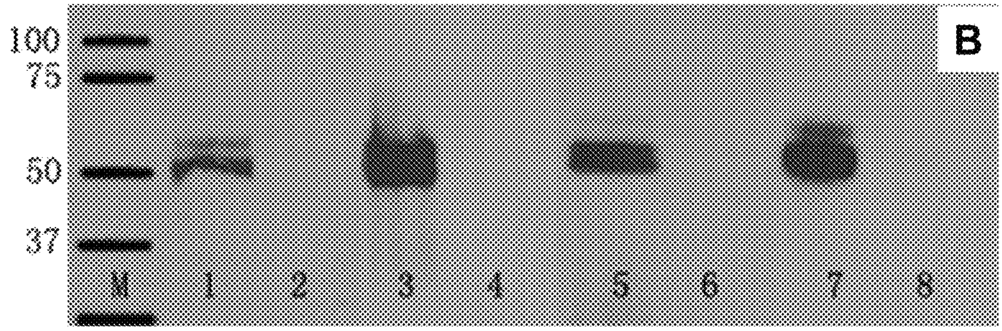
FIG. 1B illustrates Western immunoblots of gD expression. EHV-1 gD expression was detected by anti-FLAG antibodies or anti-EHV-1 gD 19-mer polyclonal antibodies. Lanes 1 and 2: cellular extracts from VC2-EHV-1-gD or VC2 infected NBL-6 cells detected by anti-FLAG antibody; lanes 3 and 4: cellular extracts from VC2-EHV-1-gD or VC2 infected Vero cells detected by anti-FLAG antibody; lanes 5 and 6: cellular extracts from VC2-EHV-1-gD, or VC2 infected NBL-6 cells detected by a rabbit antibody generated against a 19 amino acid peptide of EHV-1 gD; lanes 7 and 8: cellular extracts from VC2-EHV-1-gD and VC2 infected Vero cells detected by the anti-EHV-1 gD (19-mer).
Figure 2A:
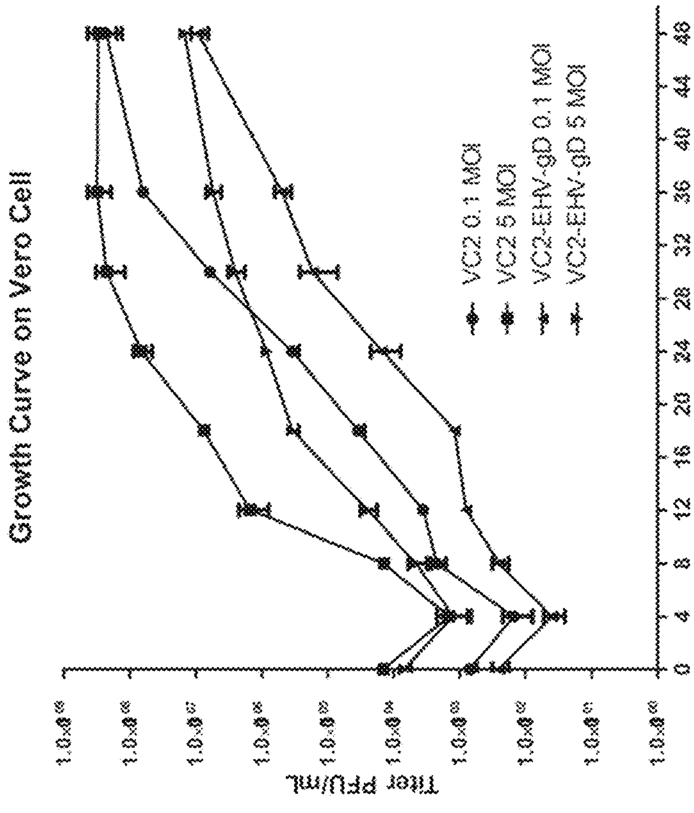
FIG. 2A is a graph illustrating replication kinetics of VC2 versus VC2-EHV-1-gD viruses. Replication kinetics were produced for VC2 and VC2-EHV-1-gD at both high (5) and low (0.1) MOI on Vero cells.
Figure 2B:
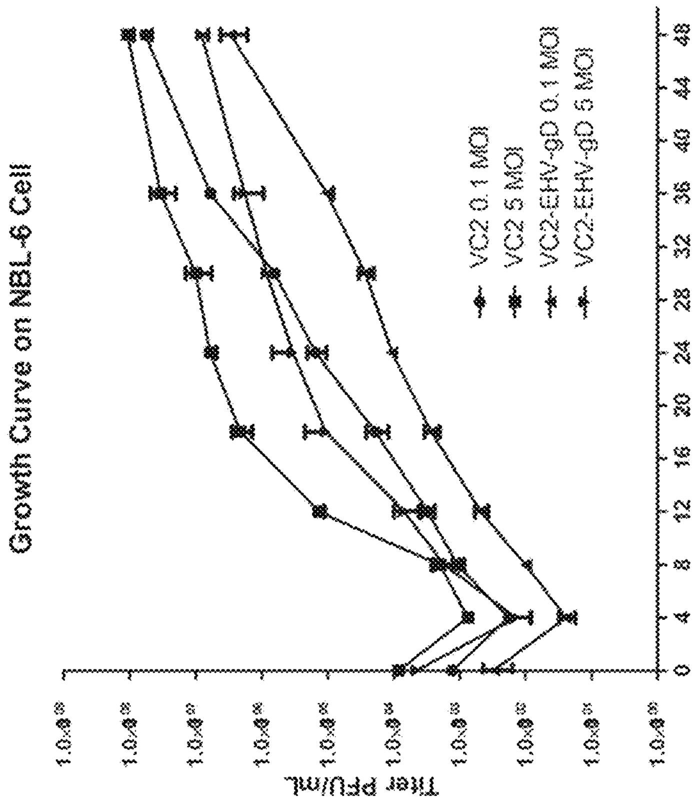
FIG. 2B is a graph illustrating replication kinetics of VC2 versus VC2-EHV-1-gD viruses. Replication kinetics were produced for VC2 and VC2-EHV-1-gD at both high (5) and low (0.1) MOI on NBL-6 cells.
Figure 3:
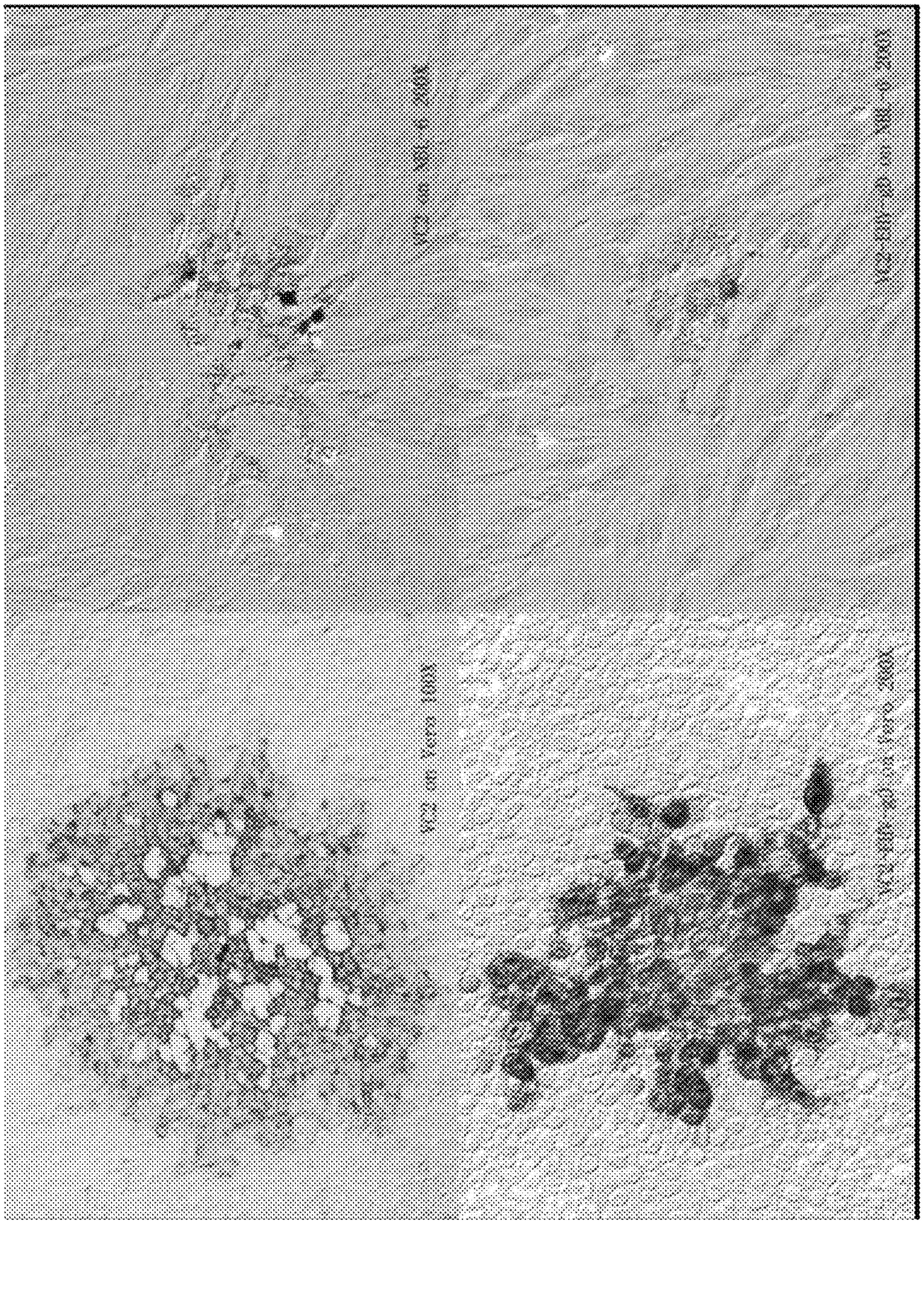
FIG. 3 is a series of digital images illustrating plaque morphology of VC2 vs VC2-EHV-gD on Vero and NBL-6 cells 72 hours post infection. Both viruses grow on Vero and NBL-6 cells and VC2-EHV-gD produces smaller plaque than VC2.

Construction and Characterization of the VC2-EHV-1-gD Vaccine:

The EHV-1 gD gene under the control of the human cytomegalovirus immediate early promoter was inserted in-place of the thymidine kinase (UL23) gene (FIG. 1A). The gene insertion was verified by PCR-assisted sequencing of the insertion site, as well as by complete genomic sequencing of parental and mutant viral genomes (not shown) to ensure the absence of any spurious mutations. The virus was able to express the EHV-1 gD efficiently in both Vero and NBL-6 infected cell extracts, as detected by both anti-gD-specific antibody and anti-FLAG antibody in western immunoblots (FIG. 1B). The VC2-EHV-1-gD virus replicated efficiently in both Vero and equine NBL-6 cells approaching similar titers at 48 hpi for both low (0.1) and high (5) MOI (FIGS. 2A and 2B). However, the VC2-EHV-1-gD virus replicated significantly slower than the parental VC2 virus reflected in their relative plaque sizes produced at 48 hpi (FIG. 3).

Figure 4:
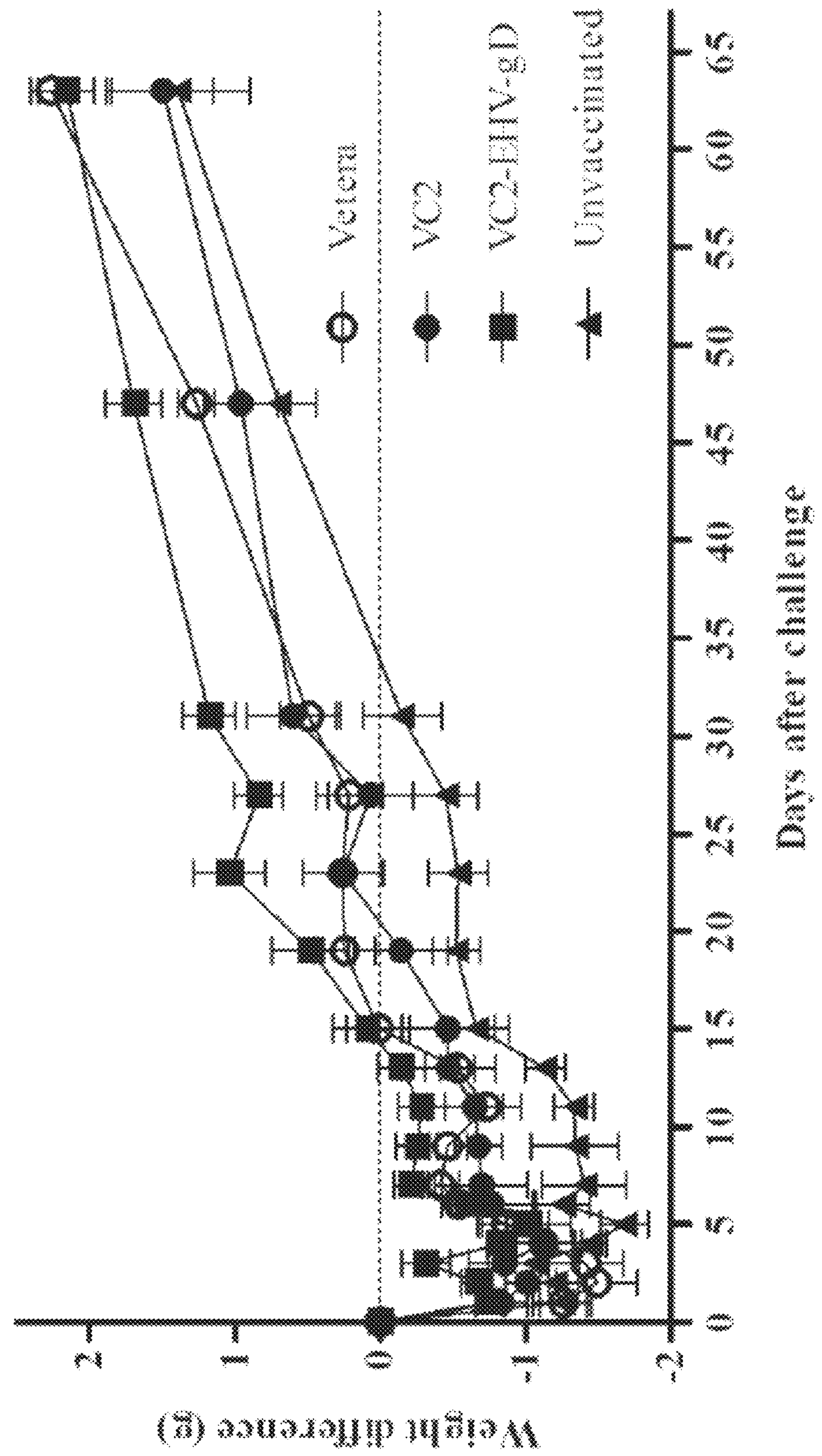
FIG. 4 is a graph illustrating the effect of vaccination on mice weights. Mice weight changes after challenge with EHV-1 clinical isolate in the Vetera, VC2, VC2-EHV-1-gD and unvaccinated groups, which were monitored daily. Statistics analyses were performed on VC2-EHV-1-gD vs Unvaccinated: Day 7*, Day 9**, Day 11*, Day23**, Day 27*, Day 31* (One-way ANOVA followed by Newman-Keuls Multiple Comparison Test *$p<0.05$, **$p<0.01$).

Monitoring of Clinical Disease Symptoms:

It has been previously reported that the parental VC2 vaccine strain did not produce any significant clinical disease after intramuscular administration in mice (Stanfield et al., (2014) *PLoS One* 9:e109890). Similarly, there were no adverse clinical signs noted by either the VC2 or the VC2-EHV-1-gD after intramuscular injection of mice throughout the vaccination period (8 weeks). In addition, there were no significant weight differences during the vaccination period among the groups (data not shown). The mice of all groups started to exhibit weight loss after challenge with wild type EHV-1, although no clinical signs such as fur ruffling and heavy breathing were observed during the 6-week interval post challenge. The unvaccinated group regained weight slower than other three groups (FIG. 4).

Characterization of Humoral Immune Responses:

Antisera from all groups of mice were individually tested at 1:20 dilution. Boost vaccination increased serum neutralization significantly. The Vetera, VC2 and VC2-EHV-1-gD vaccinated animal groups exhibited significantly higher virus neutralization activities than the unvaccinated group after the first immunization. VC2-EHV-1-gD vaccination increased virus neutralizing (VN) activities (33.6%) in mice after three consecutive vaccinations and was similar to the commercial whole virus vaccine (32.6%).

Overall, the Vetera and VC2-EHV-1-gD-vaccinated groups exhibited similar virus neutralization activities during the entire vaccination period that were significantly higher than those produced by the unvaccinated group ($p<0.01$ or $p<0.001$) and VC2 group at week 8 ($p<0.01$) (FIG. 5). Serum obtained from the VC2-EHV-1-gD immunized group generated strong antigen-specific signals (FIG. 6A), which was significantly higher than those produced by the Vetera vaccinated group ($p<0.01$), unvaccinated group and VC2 vaccinated groups ($p<0.001$).

Figure 7:
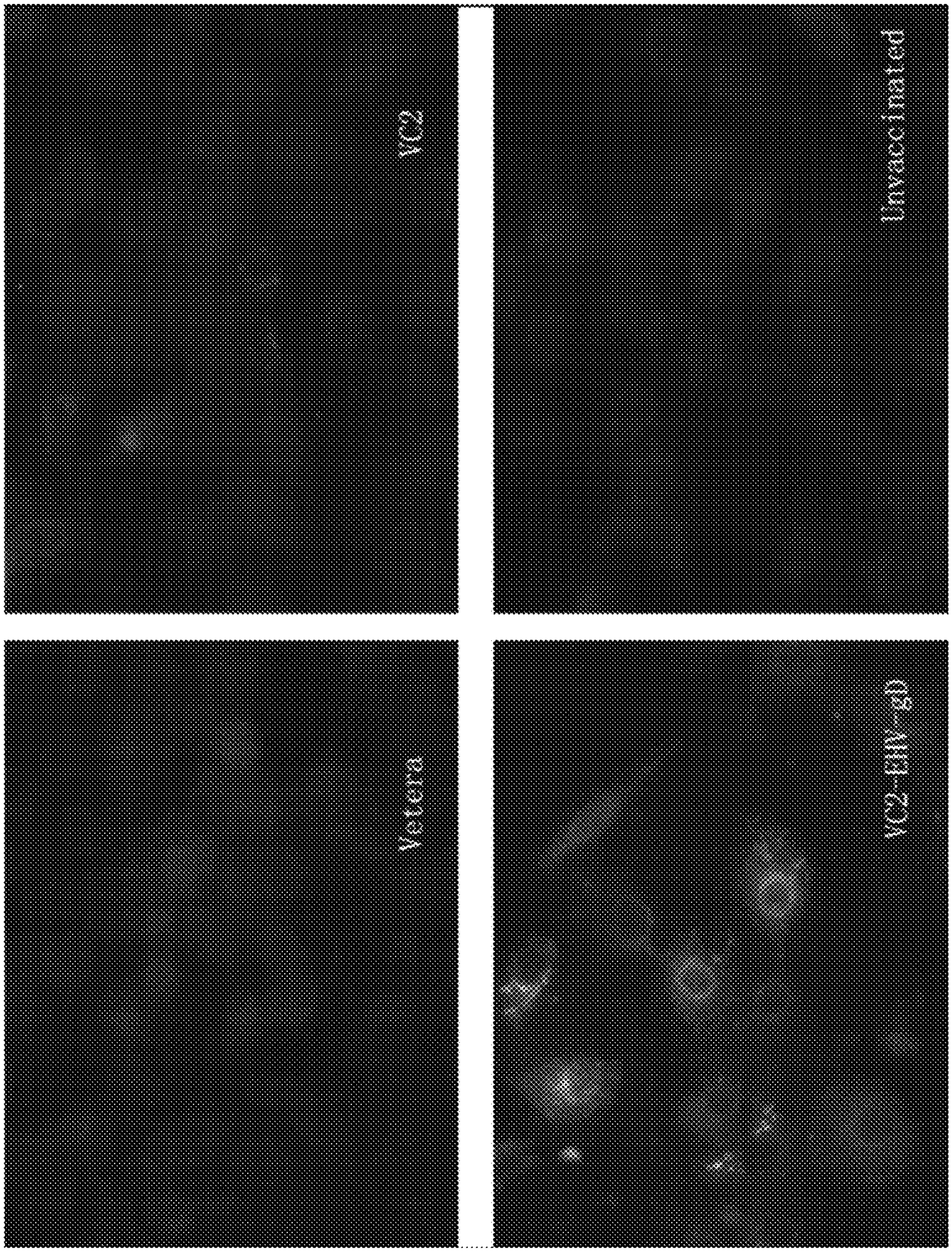
FIG. 7 is a series of digital images illustrating an anti-EHV-1 IFA assay. Mouse sera from the Vetera, VC2, VC2-EHV-1-gD and unvaccinated mice groups before challenge were diluted at 1:20 and tested by IFA assay.
Figure 8:
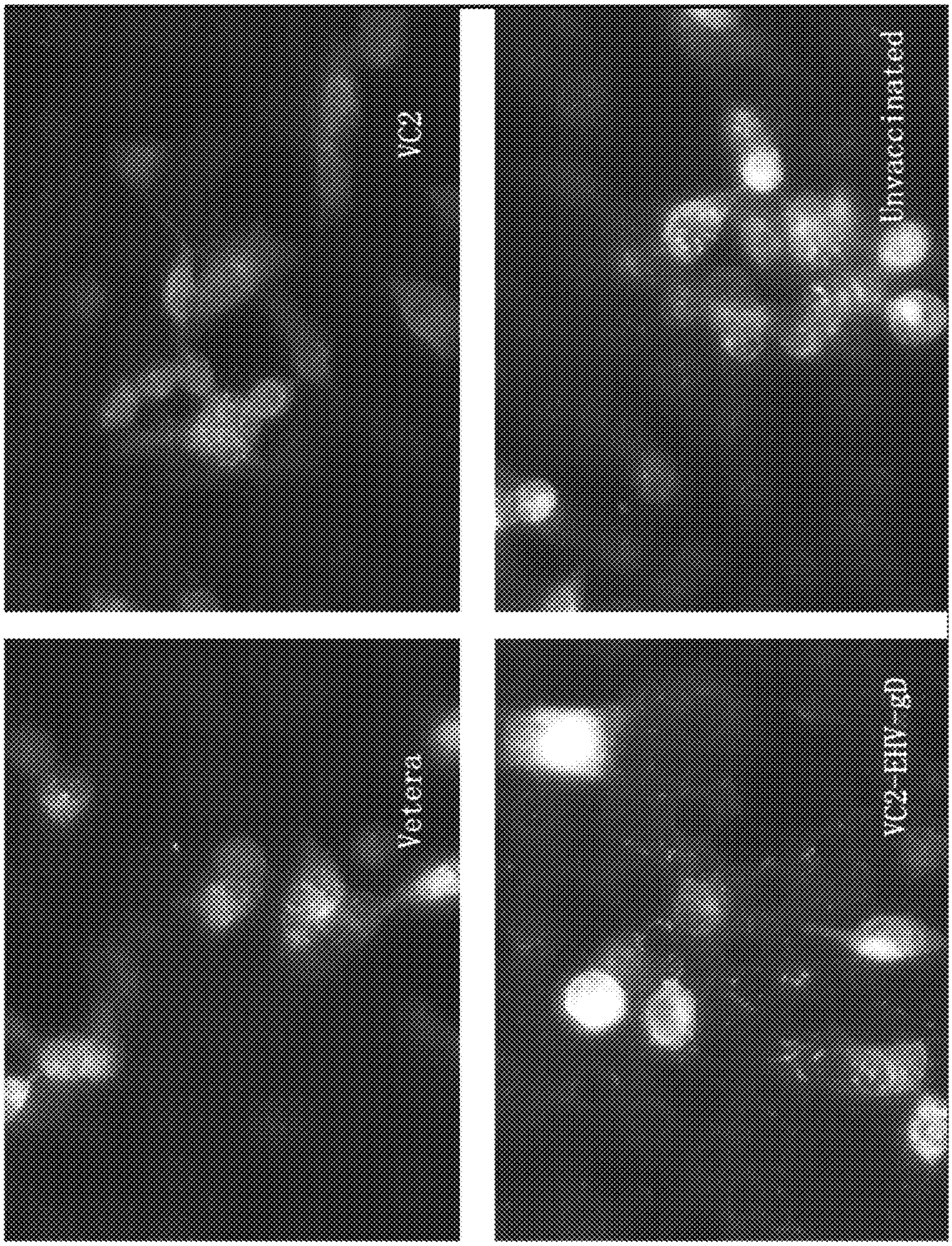
FIG. 8 is a series of digital images illustrating an anti-EHV-1 IFA assay. Mouse sera from the Vetera, VC2, VC2-EHV-1-gD and unvaccinated mice groups after challenge were diluted at 1:20 and tested by IFA assay.

Sera from all animals were also tested for their ability to detect EHV-1 antigens in Vero and NBL-6 infected cells. Sera from VC2 vaccinated animals demonstrated a higher reactivity obtained by indirect immunofluorescence to assess the ability of sera from vaccinated and unvaccinated animals to detect EHV-1 antigens in Vero and NBL-6 cells (FIG. 7). Overall, the VC2-EHV-1-gD-immunized group produced the strongest EHV-1 specific IgG antibody signals in comparison to all other sera (FIG. 6B) in agreement with the IFA-facilitated detection of EHV-1 antigens in Vero and NBL-6 infected cells (FIG. 8).

Figure 9A:
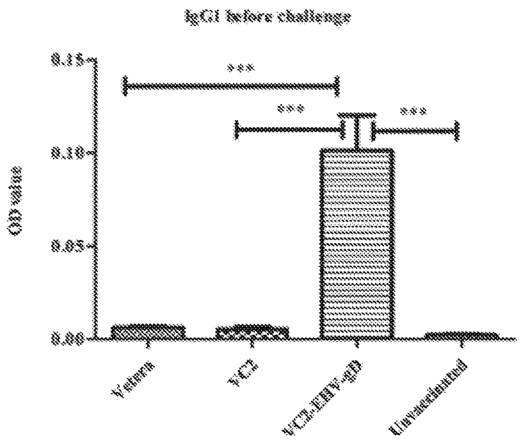
FIGS. 9A-9H is a series of graphs illustrating in vitro analysis of humoral immune response from experimental groups. Colorimetric ELISA based on analysis of EHV-1 reactive polyclonal IgG1, IgG2a, IgG2b and IgM at a 1:100 dilution of sera from the Vetera, VC2, VC2-EHV-1-gD and unvaccinated mice produced 8 weeks after first vaccination and 1 week after challenge. Statistical comparisons were conducted using one-way ANOVA followed by Newman-Keuls Multiple Comparison Test (*$p<0.05$, $p<0.01$, *$p<0.001$).
Figure 9B:
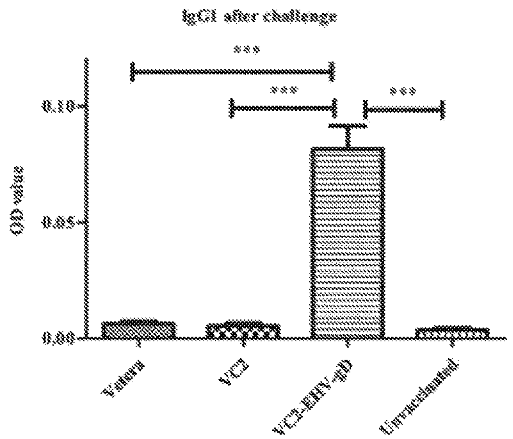
Figure 9C:
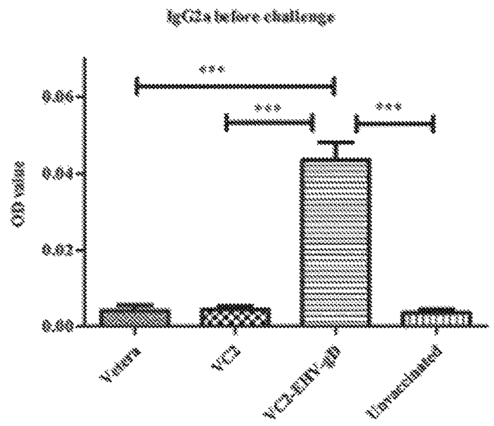
Figure 9D:
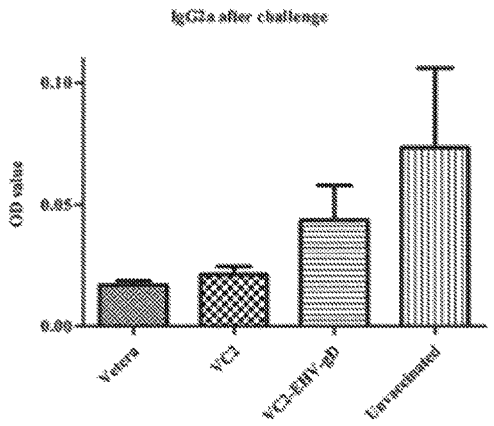
Figure 9E:
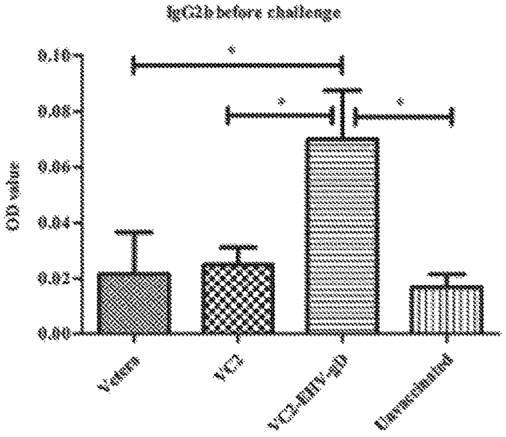
Figure 9F:
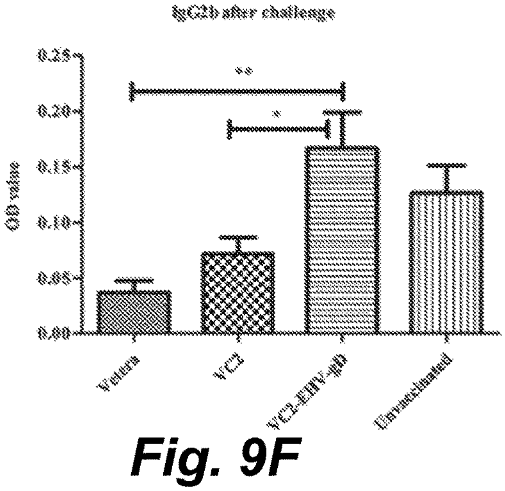
Figure 9G:
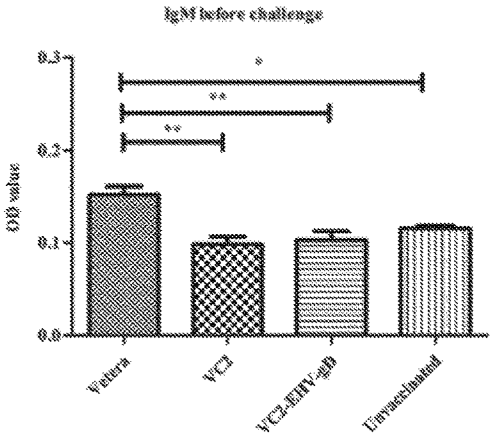
Figure 9H:
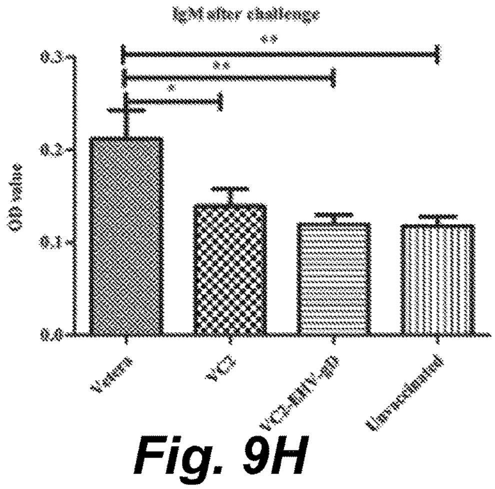
Figure 10B:
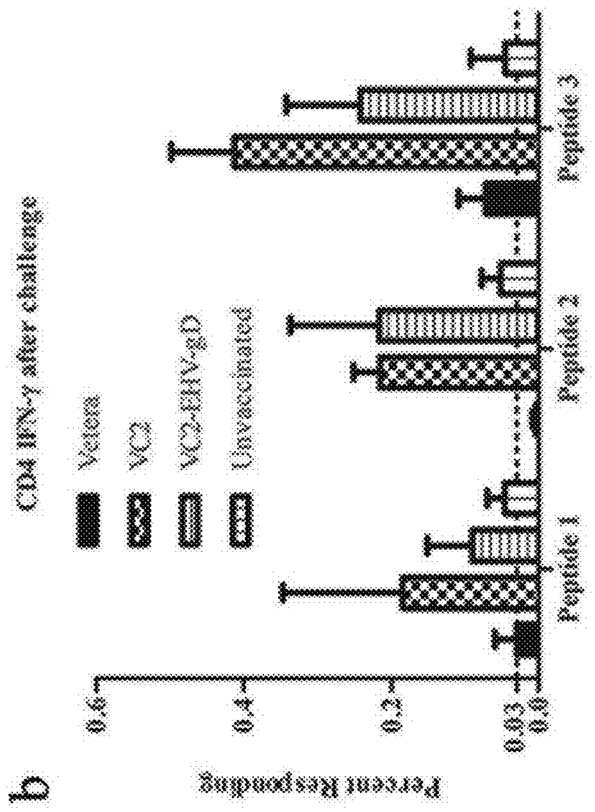
FIG. 10B is a graph illustrating in vitro analysis of mouse splenocytes $CD4^+$ cellular immune response from experimental groups analyzed by flow cytometry after stimulation by EHV-1 gD peptides.
Figure 10A:
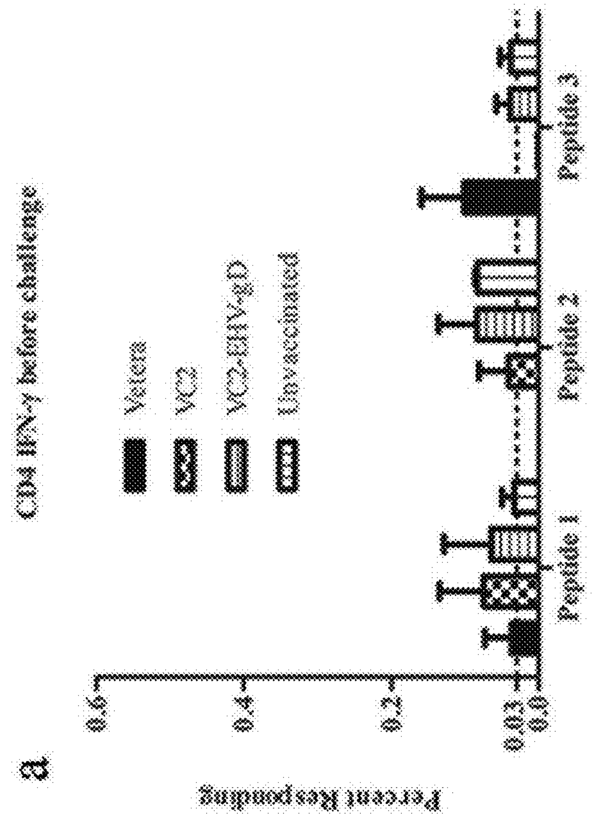
FIG. 10A is a graph illustrating in vitro analysis of mouse splenocytes $CD4^+$ cellular immune response from experimental groups analyzed by flow cytometry before stimulation by EHV-1 gD peptides.
Figure 10D:
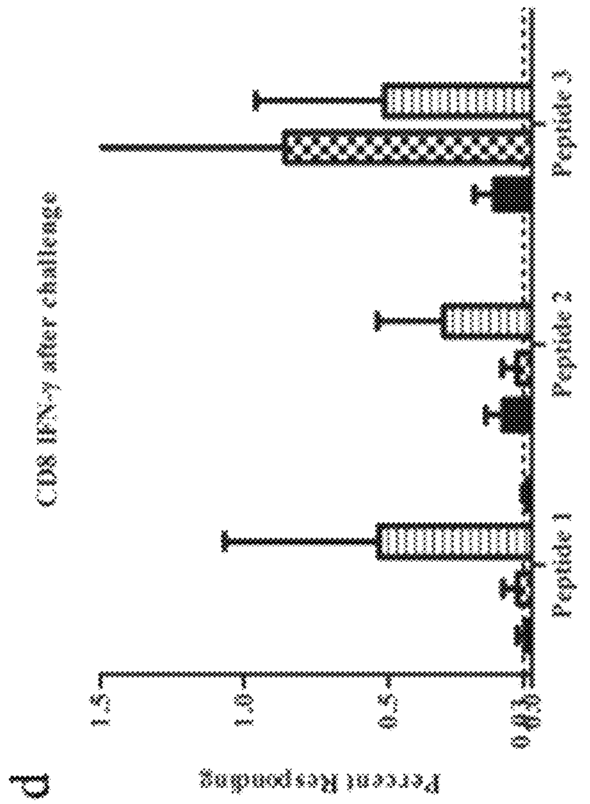
FIG. 10D is a graph illustrating in vitro analysis of mouse splenocytes $CD8^+$ cellular immune response from experimental groups analyzed by flow cytometry after stimulation by EHV-1 gD peptides.
Figure 10C:
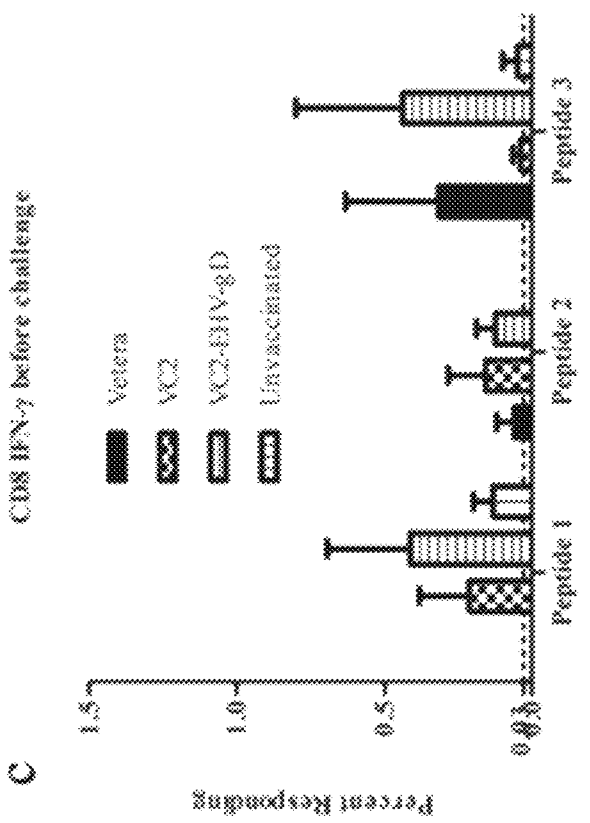
FIG. 10C is a graph illustrating in vitro analysis of mouse splenocytes $CD8^+$ cellular immune response from experimental groups analyzed by flow cytometry before stimulation by EHV-1 gD peptides.
Figure 11B:
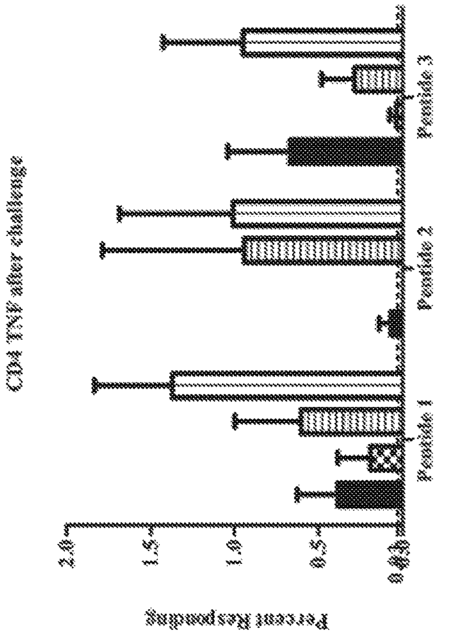
FIG. 11B is a graph illustrating in vitro analysis of cellular immune response from experimental groups. Mouse splenocytes $CD4^+$ T cells from mice from the Vetera, VC2, VC2-EHV-1-gD and unvaccinated groups after stimulation by EHV-1 gD peptides and analyzed by flow cytometry.
Figure 11A:
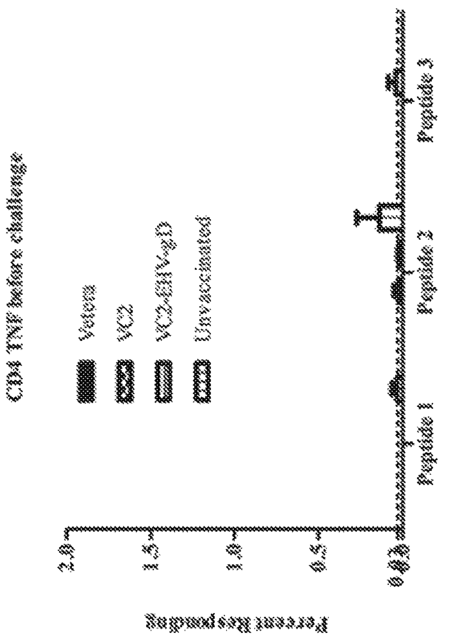
FIG. 11A is a graph illustrating in vitro analysis of cellular immune response from experimental groups. Mouse splenocytes $CD4^+$ T cells from mice from the Vetera, VC2, VC2-EHV-1-gD and unvaccinated groups before stimulation by EHV-1 gD peptides and analyzed by flow cytometry.
Figure 11D:
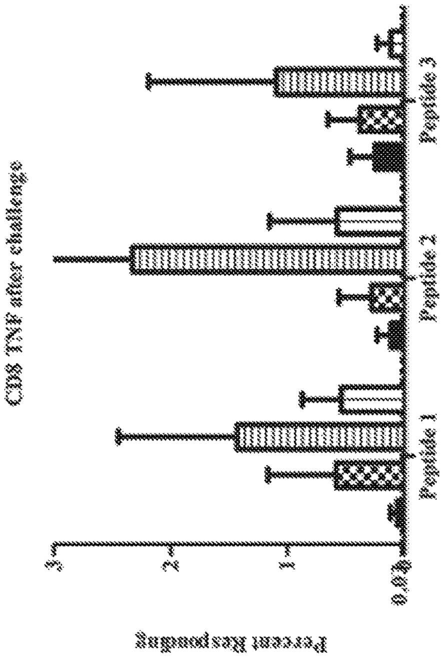
FIG. 11D is a graph illustrating in vitro analysis of cellular immune response from experimental groups. Mouse splenocytes $CD8^+$ T cells from mice from the Vetera, VC2, VC2-EHV-1-gD and unvaccinated groups after stimulation by EHV-1 gD peptides and analyzed by flow cytometry.
Figure 11C:
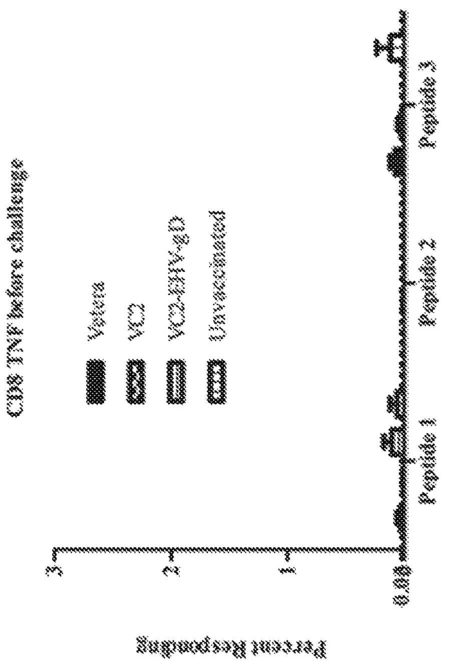
FIG. 11C is a graph illustrating in vitro analysis of cellular immune response from experimental groups. Mouse splenocytes $CD8^+$ T cells from mice from the Vetera, VC2, VC2-EHV-1-gD and unvaccinated groups before stimulation by EHV-1 gD peptides and analyzed by flow cytometry.

IgG1 levels produced in mice vaccinated with VC2-EHV-1-gD were significantly higher than other groups after three vaccinations and after challenge (FIGS. 9A and 9B, $p<0.001$). IgG2a in VC2-EHV-1-gD-vaccinated group was also significantly higher than other groups after three vaccinations (FIGS. 9C and 9D, $p<0.001$), but there was no significant difference after EHV-1 challenge. Significantly more IgG2b was produced by the VC2-EHV-1-gD group than the other groups ($p<0.05$) after three vaccinations (FIGS. 9*e* and 9*f*, $p<0.01$ or $P<0.05$). Interestingly, Vetera vaccinated animals produced significantly higher IgM levels than the other groups before and after challenge (FIGS. 9G and 9H, $p<0.01$ or $P<0.05$). No IgG3 or IgA was detected at the 1:100 dilution of sera from all treatment groups.

Cellular Immune Responses:

A surface and intercellular labeling assay was utilized to detect IFN-γ and TNF synthesized by $CD4^+$ and $CD8^+$ T cells in the presence of specific peptides (Table 2) predicted as MHC-1 or MHC-2 binding epitopes. All 3 peptides stimulated more IFN-γ producing $CD4^+$ cells in the VC2 and VC2-EHV-1-gD-vaccinated groups than the Vetera and control groups after EHV-1 challenge. There were more IFN-γ producing $CD8^+$ T cells in the VC2-EHV-1-gD-vaccinated group stimulated by peptide 1 or 3 after three vaccinations. Also, peptide 3 stimulated more IFN-γ producing $CD8^+$ in Vetera vaccinated group (FIG. 10). Moreover, all 3 peptides stimulated more IFN-γ producing $CD8^+$ cells in VC2-EHV-1-gD group after EHV-1 challenge. The peptides stimulated cellular immune response after three vaccinations and post challenge. There was more TNF producing $CD8^+$ T cells in the VC2-EHV-1-gD-vaccinated group after stimulation of peripheral blood mononuclear cells (PBMCs) by all peptides (1, 2 and 3) one-week post challenge (FIGS. 11A-11D).

Figure 12A:
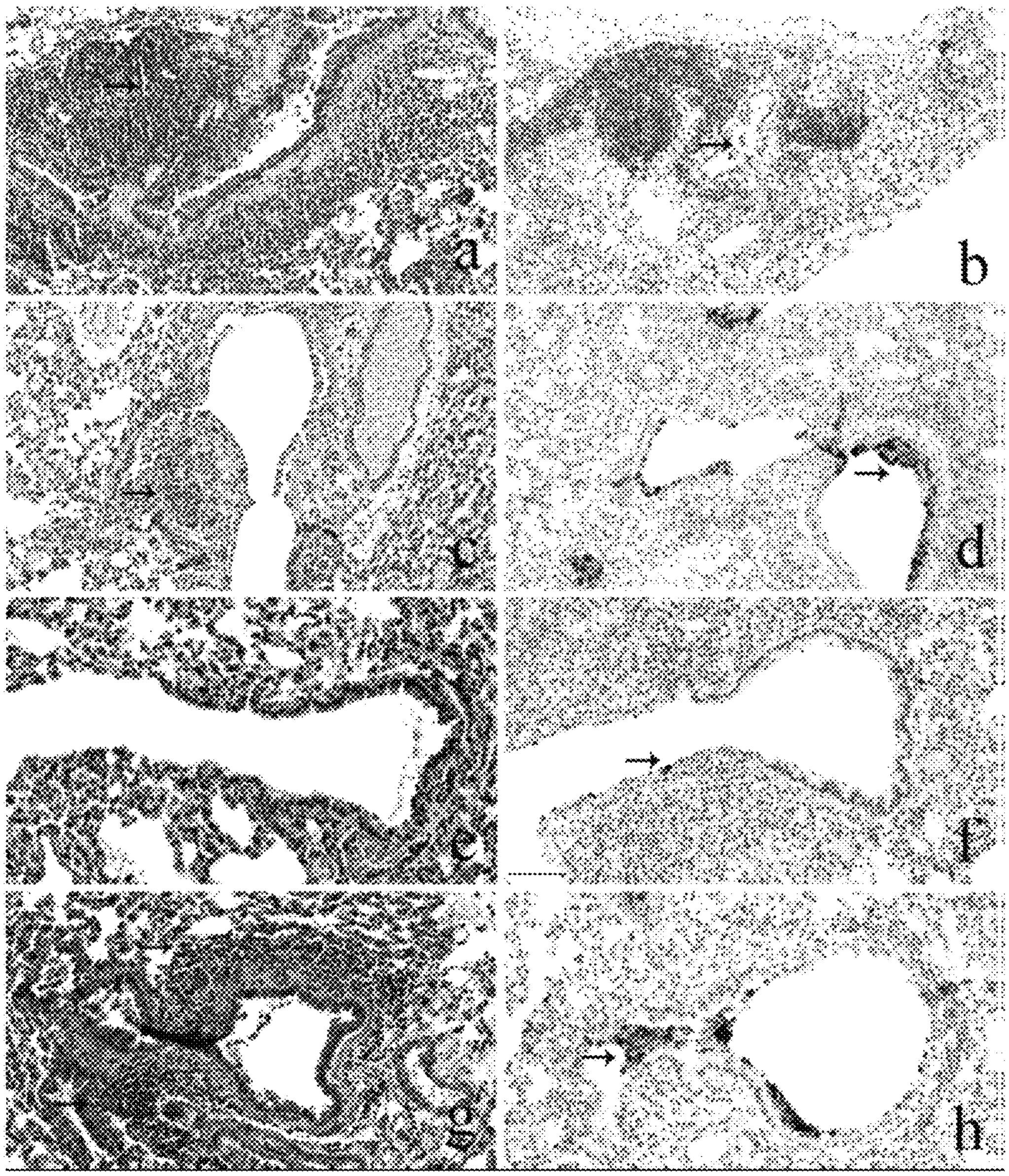
FIG. 12A is a series of digital images illustrating the histopathology of lung tissues. Lung tissue showed intense inflammatory reaction (arrows) in the peri-bronchiolar and peri-vascular areas in the lung parenchyma at day 4 post-challenge. Panels a, c, e, and g on the left side of the figure represent HE-stained samples from the Vetera (Panel a), VC2 (Panel c), VC2-EHV-1-gD (Panel e) and unvaccinated (Panel g) groups; The right side panels (Panels b, d, f, and h) show IHC staining from the Vetera (Panel b), VC2 (Panel d), VC2-EHV-1-gD (Panel f) and unvaccinated (Panel h) groups. IHC analysis shows that EHV-1 antigens were present in the infected bronchiolar cells lining the bronchioles (h, arrows). However, lung tissues of gD-vaccinated mice appear histologically normal without appreciable amounts viral antigens detected (Panel f, arrows). Photomicrographs were captured under 200× magnification.
Figure 12C:
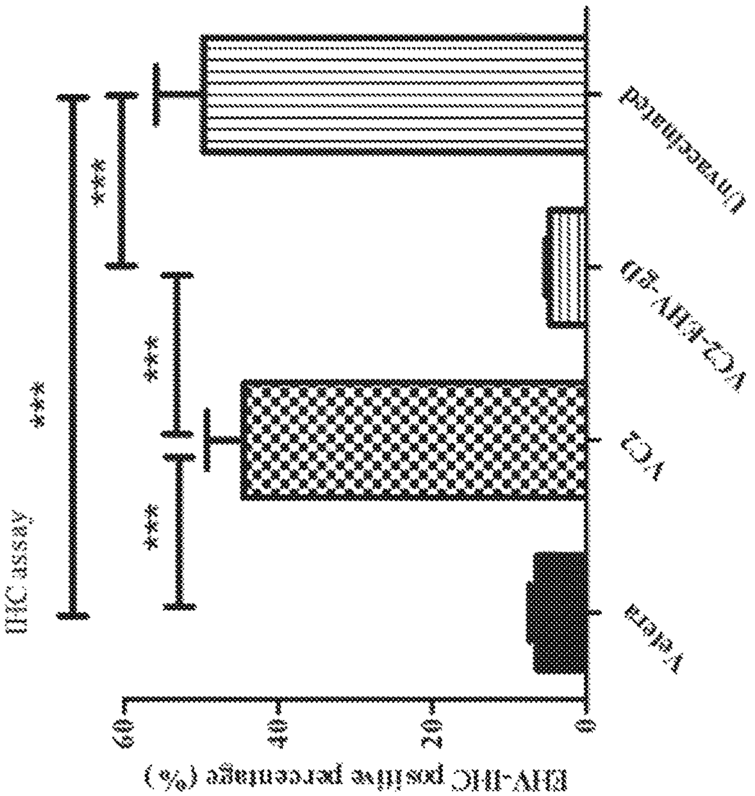
FIG. 12C is a graph illustrating the histopathology quantification. IHC staining was quantified as percentage of EHV-1 positive bronchiolar epithelial cells in lungs as described in methods (n=3 mice/group).
Figure 12B:
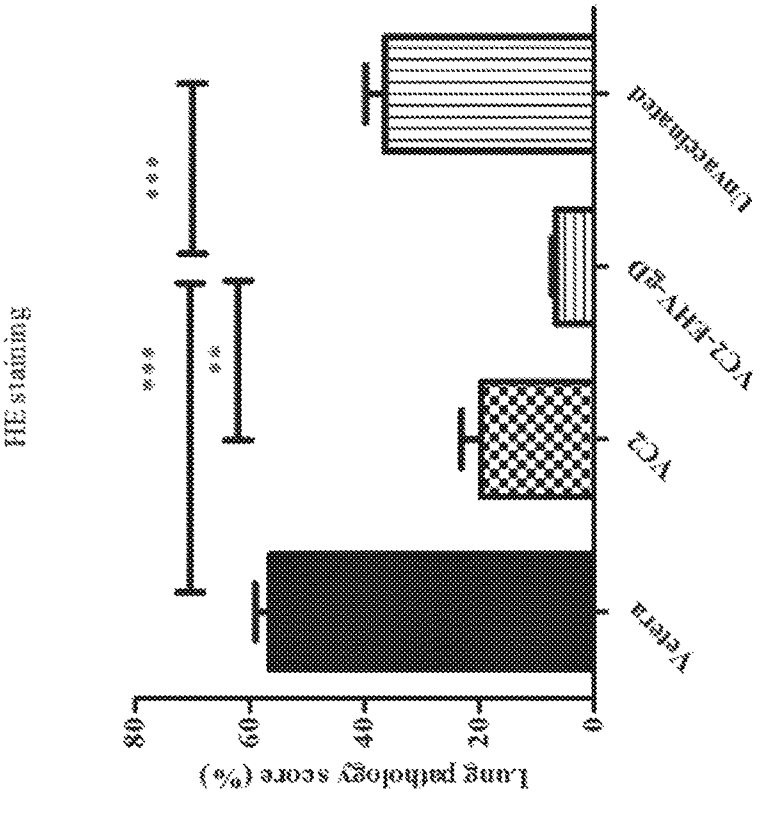
FIG. 12B is a graph illustrating the histopathology quantification. The degree of pulmonary inflammation in H&E images was quantified as pathology score (percentage) as described in methods (n=3 mice/group).

Immunohistochemistry of Mice Lung Tissues:

Immunohistochemical analysis of the lung sections revealed significant absence of EHV-1 viral antigen in the bronchiolar epithelial cells of Vetera and VC2-EHV-1-gD-vaccinated groups at 4 days post-EHV-1 challenge (FIGS. 12A-12C). However, lung tissues of unvaccinated and VC-2 vaccinated groups showed prolonged presence of EHV-1 antigen during the time period post challenge. Histopathological analysis showed that unlike the Vetera-vaccinated group, pulmonary bronchioles and vasculature in VC2-EHV-1-gD vaccinated group were surrounded by reduced level of inflammation on 4 days post challenge in comparison to the VC2 and unvaccinated groups (FIGS. 12A-12C).

Example 3

TABLE 1

Oligonucleotide primers used in this study

| Primers | Template | Sequence | SEQ ID NO |
|---|---|---|---|
| P1 | EHV-1 gD | AAGCTTGCGGCCGCGATGTCTACC TTCAAGCTTATG | 1 |
| P2 | EHV-1 gD | AAGCTTGGATCCCGGAAGCTGGGT ATATTTAAC | 2 |
| P3 | pEPkan-S | CTTGGTGAATTCAACTTCCCACAA GGAGAGCATATGACATGGTTGAAG TTCTGAGGATGACGACGATAAGTA GGG | 3 |

TABLE 1-continued

Oligonucleotide primers used in this study

| Primers | Template | Sequence | SEQ ID NO |
|---|---|---|---|
| P4 | pEPkan-S | CTTGGTGAATTCCAACCAATTAAC CAATTCTGATTAG | 4 |
| P5 | CMV-14 | GTGGCGTGAAACTCCCGCACCTCT TCGGCAAGCGCCTTGTAGAAGCGC GTCCATGTTGACATTGATTATTGA C | 5 |
| P6 | CMV-14 | TTATTGCCGTCATAGCGCGGGTTC CTTCCGGTATTGTCTCCTTCCGTG TTAAGGACAGGGAAGGGAGCAGTG G | 6 |
| P7 | EHV-1 gD | GGCGTGTACGGTGGGAGGTCTATA | 7 |
| P8 | EHV-1 gD | ATGCCAACGTGTGCAACGCCTATA | 8 |
| P9 | EHV-1 gD | TTATGAAGCCCAGGCATTCGCAAG | 9 |
| P10 | EHV-1 gD | AATTATGCCAACGTGTGCAACGC | 10 |
| P11 | EHV-1 gD | CTGGTTCGTCTACGATGGTGGAA | 11 |
| P12 | EHV-1 gD | AAGTCTGCACAGAACGGCTTGAC | 12 |

TABLE 2

MHC-1 and MHC-2 of BALB/c mouse binding prediction peptides

| | | Allele | Length | Position | Peptide | SEQ ID NO. |
|---|---|---|---|---|---|---|
| 1 | MHC-1 | H-2-Dd | 12 | 338-349 | KPPKTSKSNS TF | 13 |
| 2 | MHC-1 | H-2-Ld | 10 | 47-56 | FPPPRYNYTI | 14 |
| 3 | MHC-2 | H2-IEd | 15 | 365-379 | GVILYVCLRR KKELK | 15 |

TABLE 3

Vaccination design

| Group | # of mice | Vaccine | Dose |
|---|---|---|---|
| 1 | 15 | Naïve | No vaccination |
| 2 | 15 | Vetera ® $EHV^{XP}$ 1/4 | 0.1 ml primary, secondary, and third boost |
| 3 | 15 | VC2 | $10^5$ PFU primary, secondary, and third boost |
| 4 | 15 | VC2-EHV- | $10^5$ PFU primary, secondary, and third boost |

Vetera.RTM $EHV^{XP}$ 1/4 (Boehringer Ingelheim Vetmedica) is an inactivated virus vaccine and was diluted as 1:1000 in DMEM and 0.1 ml was used as single dose in mice.

I claim:

1. A recombinant nucleic acid comprising a nucleotide sequence encoding a live-attenuated chimeric Herpes Simplex Virus Type-1 (HSV-1) VC2 virus and a nucleotide sequence encoding a heterologous polypeptide operably linked to a promoter, wherein the nucleotide sequence encoding the heterologous polypeptide operably linked to a promoter encodes the glycoprotein D (gD) of Equine Herpesvirus-1 (EHV-1) or a fragment thereof.

2. A live-attenuated recombinant Herpes Simplex Virus Type-1 (HSV-1) VC2 virus comprising a nucleotide sequence encoding a nucleotide sequence encoding a heterologous polypeptide operably linked to a promoter, wherein the nucleotide sequence encoding the heteroloqous polypeptide operably linked to a promoter encodes the glycoprotein D (gD) of Equine Herpesvirus-1 (EHV-1) or a fragment thereof.

3. A viral vaccine comprising a physiologically acceptable carrier and an immunogenic amount of a chimeric Herpes Simplex Virus Type-1 (HSV-1) VC2 virus comprising a nucleotide sequence encoding a heterologous polypeptide operably linked to a promoter, wherein the nucleotide sequence encoding the heteroloqous polypeptide operably linked to a promoter encodes the glycoprotein D (gD) of Equine Herpesvirus-1 (EHV-1) or a fragment thereof.

4. The viral vaccine of claim 3 wherein the physiologically acceptable carrier comprises an adjuvant.

5. A method of generating an antibody in an animal, wherein said method comprises the step of administering to an animal a pharmaceutically acceptable composition comprising a chimeric live-attenuated Herpes Simplex Virus Type-1 (HSV-1) VC2 virus, said virus comprising a nucleotide sequence encoding a heterologous polypeptide operably linked to a promoter, and a physiologically acceptable carrier, wherein the nucleotide sequence encoding the heterologous polypeptide operably linked to a promoter encodes the glycoprotein D (gD) of Equine Herpesvirus-1 (EHV-1) or a fragment thereof.

6. A method of generating an immune response in an animal, wherein said method comprising the step of administering to an animal a pharmaceutically acceptable composition comprising a chimeric live-attenuated Herpes Simplex Virus Type-1 (HSV-1) VC2 virus, said virus comprising a nucleotide sequence encoding a heterologous polypeptide operably linked to a promoter, and a physiologically acceptable carrier, wherein the nucleotide sequence encoding the heterologous polypeptide operably linked to a promoter encodes the glycoprotein D (gD) of Equine Herpesvirus-1 (EHV-1) or a fragment thereof.

* * * * *